United States Patent
Ackermann et al.

(10) Patent No.: US 7,345,067 B2
(45) Date of Patent: Mar. 18, 2008

(54) ANILINE DERIVATIVES, THEIR MANUFACTURE AND USE AS PHARMACEUTICAL AGENTS

(75) Inventors: Jean Ackermann, Riehen (CH); Johannes Aebi, Basel (CH); Alfred Binggeli, Binningen (CH); Uwe Grether, Loerrach (DE); Georges Hirth, Huningue (FR); Bernd Kuhn, Riehen (CH); Hans-Peter Maerki, Basel (CH); Markus Meyer, Neuenburg (DE); Peter Mohr, Basel (CH); Matthew Blake Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 500 days.

(21) Appl. No.: 10/858,297

(22) Filed: Jun. 1, 2004

(65) Prior Publication Data
US 2004/0248951 A1 Dec. 9, 2004

(30) Foreign Application Priority Data
Jun. 6, 2003 (EP) ................................. 03012210
Nov. 19, 2003 (EP) ................................. 03026443

(51) Int. Cl.
*A61K 31/426* (2006.01)
*C07D 277/20* (2006.01)

(52) U.S. Cl. ..................... 514/365; 548/146; 548/202; 548/203; 548/204

(58) Field of Classification Search ................ 548/646, 548/202, 203, 204; 514/365
See application file for complete search history.

(56) References Cited

U.S. PATENT DOCUMENTS

| | | |
|---|---|---|
| 6,548,538 B2 | 4/2003 | Urbahns et al. |
| 6,750,236 B2 | 6/2004 | Urbahns et al. |
| 2003/0032671 A1 | 2/2003 | Urbahns et al. |
| 2003/0187041 A1 | 10/2003 | Urbahns et al. |
| 2004/0176445 A1 | 9/2004 | Urbahns et al. |

FOREIGN PATENT DOCUMENTS

| | | |
|---|---|---|
| DE | 101 24 905 A1 | 4/2002 |
| WO | WO 97/27857 A1 | 8/1997 |
| WO | WO 02/28433 A2 | 4/2002 |
| WO | WO 02/062774 A1 | 8/2002 |
| WO | WO 02/081454 A1 | 10/2002 |
| WO | WO 03 072100 | 9/2003 |
| WO | WO 03 072102 | 9/2003 |

*Primary Examiner*—Golam M. M. Shameem
(74) *Attorney, Agent, or Firm*—George W. Johnston; Dennis P. Tramaloni; Brian C. Remy

(57) ABSTRACT

This invention relates to compounds of the formula

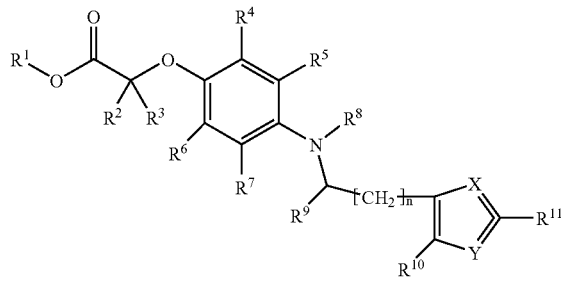

I wherein
X is N and Y is S or O; or
X is S or O and Y is N;
$R^1$ is hydrogen or $C_{1-7}$-alkyl;
$R^2$ and $R^3$ independently from each other are selected from the group consisting of hydrogen, $C_{1-7}$-alkyl and $C_{1-7}$-alkoxy;
$R^4$, $R^5$, $R^6$, and $R^7$ independently from each other are selected from the group consisting of hydrogen, $C_{1-7}$-alkyl, $C_{3-7}$-cycloalkyl, halogen, $C_{1-7}$-alkoxy, $C_{1-7}$-alkyl-$C_{1-7}$-alkoxy-$C_{1-7}$-alkyl, $C_{2-7}$-alkenyl, $C_{2-7}$-alkinyl, fluoro-$C_{1-7}$-alkyl and cyano;
$R^8$ is selected from the group consisting of hydrogen, $C_{1-7}$-alkyl, $C_{3-7}$-cycloalkyl and fluoro-$C_{1-7}$-alkyl;
$R^9$ is selected from the group consisting of hydrogen, $C_{1-7}$-alkyl, $C_{2-7}$-alkinyl, $C_{3-7}$-cycloalkyl and fluoro-$C_{1-7}$-alkyl;
$R^{10}$ is selected from the group consisting of hydrogen, $C_{1-7}$-alkyl, $C_{2-7}$-alkinyl, $C_{3-7}$-cycloalkyl and fluoro-$C_{1-7}$-alkyl;
$R^{11}$ is aryl or heteroaryl;
N is 0, 1 or 2;
and all enantiomers and pharmaceutically acceptable salts and/or esters thereof and their use as PPAR activators.

19 Claims, No Drawings

ANILINE DERIVATIVES, THEIR MANUFACTURE AND USE AS PHARMACEUTICAL AGENTS

BACKGROUND OF THE INVENTION

The present invention relates to novel aniline derivatives, to a process for their manufacture, pharmaceutical compositions containing them and their manufacture as well as the use of these compounds as pharmaceutically active agents.

WO 03/072100 A1 and WO 03/072102 A1 disclose similar substituted thiazole derivatives which act as PPAR modulators.

Peroxisome Proliferator Activated Receptors (PPARs) are members of the nuclear hormone receptor superfamily. The PPARs are ligand-activated transcription factors that regulate gene expression and control multiple metabolic pathways. Three subtypes have been described which are PPARα, PPARδ (also known as PPARβ), and PPARγ. PPARδ is ubiquitously expressed. PPARα is predominantly expressed in the liver, kidney and heart. There are at least two major isoforms of PPARγ. PPARγ1 is expressed in most tissues, and the longer isoform, PPARγ2 is almost exclusively expressed in adipose tissue. The PPARs modulate a variety of physiological responses including regulation of glucose- and lipid-homeostasis and metabolism, energy balance, cell differentiation, inflammation and cardiovascular events.

Approximately half of all patients with coronary artery disease have low concentrations of plasma HDL cholesterol. The atheroprotective function of HDL was first highlighted almost 25 years ago and stimulated exploration of the genetic and environmental factors that influence HDL levels. The protective function of HDL comes from its role in a process termed reverse cholesterol transport. HDL mediates the removal of cholesterol from cells in peripheral tissues including those in the atherosclerotic lesions of the arterial wall. HDL then delivers its cholesterol to the liver and sterol-metabolizing organs for conversion to bile and elimination. Data from the Framingham study showed that HDL-C levels are predictive of coronary artery disease risk independently of LDL-C levels (Gordon et al., *Am. J. Med.* 1977, 62, 707-714). The estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial side-effects limit the therapeutic potential of this approach.

As many as 90% of the 14 million diagnosed type 2 diabetic patients in the US are overweight or obese, and a high proportion of type 2 diabetic patients have abnormal concentrations of lipoproteins. The prevalence of total cholesterol >240 mg/dl is 37% in diabetic men and 44% in women. The respective rates for LDL-C >160 mg/dl are 31% and 44%, respectively, and for HDL-C <35 mg/dl 28% and 11%, respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and afflicts 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in later stage of disease, due to exhaustion and failure of pancreatic insulin-producing capacity. Thus T2D is a cardiovascular-metabolic syndrome associated with multiple comorbidities including insulin resistance, dyslipidemia, hypertension, endothelial dysfunction and inflammatory atherosclerosis.

First line treatment for dyslipidemia and diabetes generally involves a low-fat and low-glucose diet, exercise and weight loss. However, compliance can be moderate, and as the disease progresses, treatment of the various metabolic deficiencies becomes necessary with e.g. lipid-modulating agents such as statins and fibrates for dyslipidemia and hypoglycemic drugs, e.g. sulfonylureas or metformin for insulin resistance. A promising new class of drugs has recently been introduced that resensitizes patients to their own insulin (insulin sensitizers), thereby restoring blood glucose and triglyceride levels to normal, and in many cases, obviating or reducing the requirement for exogenous insulin. Pioglitazone (Actos™) and rosiglitazone (Avandia™) belong to the thiazolidinedione (TZD) class of PPARγ-agonists and were the first in their class to be approved for NIDDM in several countries. These compounds, however, suffer from side effects, including rare but severe liver toxicity (as seen with troglitazone). They also increase body weight in patients. Therefore, new, more efficacious drugs with greater safety and lower incidence of side effects are urgently needed. Recent studies provide evidence that agonism of PPARδ would result in compounds with enhanced therapeutic potential, i.e. such compounds should improve the lipid profile, with a superior effect on HDL-C raising compared to current treatments and with additional positive effects on normalization of insulin-levels (Oliver et al; Proc Nat Acad Sci USA 2001; 98: 5306-11). Recent observations also suggest that there is a independent PPARα mediated effect on insulin-sensitization in addition to its well known role in reducing triglycerides (Guerre-Millo et al; J Biol Chem 2000; 275: 16638-16642). Thus, selective PPARδ agonists or PPARδ agonists with additional PPARα activity may show superior therapeutic efficacy without the side-effects such as the weight gain seen with PPARγ agonists.

The novel compounds of the present invention exceed the compounds known in the art, inasmuch as they bind to and selectively activate PPARδ or coactivate PPARδ and PPARα simultaneously and very efficiently, and with much improved pharmacokinetic properties. Therefore, these compounds combine the anti-dyslipidemic and anti-glycemic effects of PPARδ and PPARα activation with no effect on PPARγ. Consequently, HDL cholesterol is increased, triglycerides lowered (=improved lipid profile) and plasma glucose and insulin are reduced (=insulin sensitization). In addition, such compounds may also lower LDL cholesterol, decrease blood pressure and counteract inflammatory atherosclerosis. Furthermore, such compounds may also be useful for treating inflammatory diseases such as rheumatoid arthritis, osteoarthritis, and psoriasis. Since multiple facets of combined dyslipidemia and the T2D disease syndrome are addressed by PPARδ-selective agonists and PPARδ and α coagonists, they are expected to have an enhanced therapeutic potential compared to the compounds already known in the art.

The compounds of the present invention further exhibit improved pharmacological properties compared to known compounds.

SUMMARY OF THE INVENTION

The present invention is concerned with novel aniline derivatives of the general formula

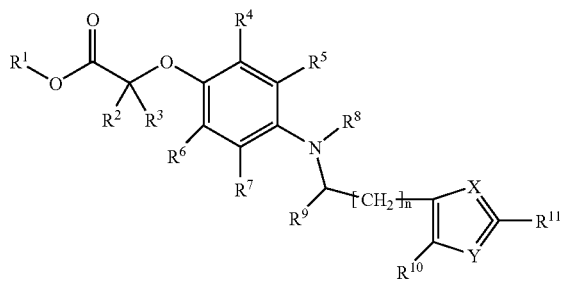

wherein

X, Y, R', $R^2$, $R^3$, $R^4$, $R^5$, $R^6$, $R^7$, $R^8$, $R^9$, $R^{10}$, $R^{11}$ and n are as described herewithin below.

It has been found that compounds of formula I are useful as lipid modulators and insulin sensitizers. In particular, compounds of formula I are PPAR activators.

DETAILED DESCRIPTION OF THE INVENTION

The present invention relates to compounds of formula (I)

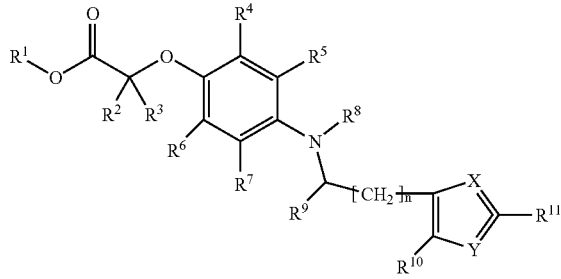

wherein

X is N and Y is S or O; or

X is S or O and Y is N;

$R^1$ is hydrogen or $C_{1-6}$-alkyl;

$R^2$, $R^3$ independently from each other are hydrogen, $C_{1-7}$-alkyl, $C_{1-7}$-alkoxy;

$R^4$, $R^5$, $R^6$ and $R^7$ independently from each other are hydrogen, $C_{1-7}$-alkyl, $C_{3-7}$-cycloalkyl, halogen, $C_{1-7}$-alkoxy, $C_{1-7}$-alkyl-$C_{1-7}$-alkoxy-$C_{1-7}$-alkyl, $C_{2-6}$-alkenyl, $C_{2-7}$-alkinyl, fluoro-$C_{1-7}$-alkyl, cyano;

$R^8$ is hydrogen, $C_{1-7}$-alkyl, $C_{3-7}$-cycloalkyl, fluoro-$C_{1-7}$-aklyl;

$R^9$ is hydrogen, $C_{1-7}$-alkyl, $C_{2-7}$-alkinyl, $C_{3-7}$-cycloalkyl, fluoro-$C_{1-7}$-alkyl;

$R^{10}$ is hydrogen, $C_{1-7}$-alkyl, $C_{2-7}$-alkinyl, $C_{3-7}$-cycloalkyl, fluoro-$C_{1-7}$-alkyl;

$R^{11}$ is aryl or heteroaryl;

n is 0, 1 or 2;

and all enantiomers and pharmaceutically acceptable salts and/or esters thereof.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the groups specifically exemplified herein.

The term "halogen" refers to fluorine, chlorine, bromine and iodine.

The term "fluoro-lower alkyl" or "fluoro-$C_{1-7}$-alkyl" refers to lower alkyl groups which are mono- or multiply substituted with fluorine. Examples of fluoro-lower alkyl groups are e.g. —$CF_3$, —$CH_2CF_3$ and —$CH(CF_3)_2$ and the groups specifically exemplified herein.

The term "alkoxy" refers to the group R'—O—, wherein R' is alkyl. The term "lower-alkoxy" or "$C_{1-7}$-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Preferred are the lower-alkoxy groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-7}$-alkinyl", alone or in combination, signifies a straight-chain or branched hydrocarbon residue comprising a triple bond and up to 7, preferably up to 6, particularly preferred up to 4 carbon atoms. Examples of alkinyl groups are ethinyl, 1-propinyl, or 2-propinyl.

The term "cycloalkyl" or "$C_{3-7}$-cycloalkyl" denotes a saturated carbocyclic group containing from 3 to 6 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono- or multiply-substituted, particularly mono- or di-substituted by halogen, hydroxy, CN, $CF_3$, $NO_2$, $NH_2$, N(H, lower-alkyl), N(lower-alkyl)$_2$, carboxy, aminocarbonyl, lower-alkyl, lower-alkoxy, aryl and/or aryloxy. Preferred substituents are halogen, $CF_3$, lower-alkyl and/or lower-alkoxy. Preferred are the specifically exemplified aryl groups. The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are e.g. thienyl and furyl which can optionally be substituted as described above, preferably with halogen, $CF_3$, lower-alkyl and/or lower-alkoxy.

The term "protecting group" refers to groups such as e.g. acyl, alkoxycarbonyl, aryloxycarbonyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The salvation can be effected in the course of the manufacturing process or can take place e.g. as a consequence of hygroscopic properties of an initially anhydrous compound of formula (I) (hydration).

The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

Preferred compounds of formula I of the present invention are those, wherein X is S and Y is N.

Furthermore, compounds of formula I wherein $R^1$ is hydrogen, are preferred.

Compounds of formula I, wherein $R^2$ and $R^3$ are hydrogen, are also preferred. Further preferred are compounds of formula I, wherein $R^4$ is hydrogen, $C_{1-7}$-alkyl, $C_{3-7}$-cycloalkyl, halogen, $C_{1-7}$-alkoxy, $C_{1-7}$-alkyl-$C_{1-7}$-alkoxy-$C_{1-7}$-alkyl, $C_{2-7}$-alkenyl, $C_{2-7}$-alkinyl, fluoro-$C_{1-7}$-alkyl or cyano, and $R^5$, $R^6$ and $R^7$ are hydrogen. More preferred are those compounds, wherein $R^4$ is hydrogen, $C_{1-7}$-alkyl, halogen, $C_{1-7}$-alkoxy or fluoro-$C_{1-7}$-alkyl, and particularly preferred are those compounds of formula I, wherein $R^4$ is $C_{1-7}$-alkyl, halogen or fluoro-$C_{1-7}$-alkyl.

Other preferred compounds of formula I according to the present invention are those, wherein $R^8$ is hydrogen or $C_{1-6}$-alkyl, with those compounds, wherein $R^8$ is methyl, being particularly preferred.

Compounds of formula I, wherein $R^9$ is hydrogen or $C_{1-7}$-alkyl, are also preferred. Further preferred compounds of formula I according to present invention are those, wherein $R^{10}$ is hydrogen or $C_{1-7}$-alkyl, with those compounds, wherein $R^{10}$ is methyl, being especially preferred.

Compounds of formula I, wherein $R^{11}$ is aryl, are preferred. More preferred are those compounds of formula I, wherein $R^{11}$ is unsubstituted phenyl or phenyl substituted with one to three groups selected from $C_{1-7}$-alkyl, $C_{1-7}$-alkoxy, halogen, fluoro-$C_{1-7}$-alkyl and cyano, with those compounds, wherein $R^{11}$ is phenyl substituted with halogen or fluoro-$C_{1-7}$-alkyl, being particularly preferred. Especially preferred are those compounds, wherein $R^{11}$ is 4-trifluoromethyl-phenyl.

Also preferred are compounds of formula I, wherein n is 0. Further preferred are compounds of formula I, wherein n is 1.

Examples of preferred compounds of formula I are the following:
(2-methyl-4-{methyl-[4-methyl-2-(4-trifluoromethyl-phenyl)-thiazol-5-ylmethyl]-amino}-phenoxy)-acetic acid,
(2-methyl-4-{methyl-[2-(4-trifluoromethyl-phenyl)-thiazol-5-ylmethyl]-amino}-phenoxy)-acetic acid,
(R, S)-[2-methyl-4-(methyl-{1-[4-methyl-2-(4-trifluoromethyl-phenyl)-thiazol-5-yl]-ethyl}-amino)-phenoxy]-acetic acid,
(2-chloro-4-{methyl-[4-methyl-2-(4-trifluoromethyl-phenyl)-thiazol-5-ylmethyl]-amino}-phenoxy)-acetic acid,
(2-fluoro-4-{methyl-[4-methyl-2-(4-trifluoromethyl-phenyl)-thiazol-5-ylmethyl]-amino}-phenoxy)-acetic acid,
(4-methyl-[4-methyl-2-(4-trifluoromethyl-phenyl)-thiazol-5-ylmethyl]-amino}-2-trifluoromethyl-phenoxy)-acetic acid,
(2-ethyl-4-{methyl-[4-methyl-2-(4-trifluoromethyl-phenyl)-thiazol-5-ylmethyl]-amino}-phenoxy)-acetic acid.
(2-methoxy-4-{methyl-[4-methyl-2-(4-trifluoromethyl-phenyl)-thiazol-5-ylmethyl]-amino}-phenoxy)-acetic acid,
(4-{ethyl-[4-methyl-2-(4-trifluoromethyl-phenyl)-thiazol-5-ylmethyl]-amino}-phenoxy)-acetic acid,
(4-{ethyl-[2-(4-trifluoromethyl-phenyl)-thiazol-5-ylmethyl]-amino}-phenoxy)-acetic acid,
(4-{[4-methyl-2-(4-trifluoromethyl-phenyl)-thiazol-5-ylmethyl]-amino}-phenoxy)-acetic acid, and
(4-{methyl-[4-methyl-2-(4-trifluoromethyl-phenyl)-thiazol-5-ylmethyl]-amino}-phenoxy)-acetic acid.

Further preferred compounds of formula I of the present invention include the following:
(2-(3-methoxy-propyl)-4-{methyl-[4-methyl-2-(4-trifluoromethyl-phenyl)-thiazol-5-ylmethyl]-amino}-phenoxy)-acetic acid,
(2-methyl-4-{[4-methyl-2-(4-trifluoromethyl-phenyl)-thiazol-5-ylmethyl]-amino}-phenoxy)-acetic acid,
(4-{ethyl-[4-methyl-2-(4-trifluoromethyl-phenyl)-thiazol-5-ylmethyl]-amino}-2,6-dimethyl-phenoxy)-acetic acid,
(2,6-dimethyl-4-{methyl-[4-methyl-2-(4-trifluoromethyl-phenyl)-oxazol-5-ylmethyl]-amino}-phenoxy)-acetic acid,
(R,S)-[2-methyl-4-(methyl-{1-[2-(4-trifluoromethyl-phenyl)-thiazol-5-yl]-ethyl}-amino)-phenoxy]-acetic acid,
(2-methyl-4-{methyl-[4-methyl-2-(4-trifluoromethyl-phenyl)-oxazol-5-ylmethyl]-amino}-phenoxy)-acetic acid, (4-{ethyl-[4-methyl-2-(4-trifluoromethyl-phenyl)-thiazol-5-ylmethyl]-amino}-2-methyl-phenoxy)-acetic acid, and
(2-iodo-4-{methyl-[4-methyl-2-(4-trifluoromethyl-phenyl)-thiazol-5-ylmethyl]-amino}-phenoxy)-acetic acid.

Particularly preferred compounds of formula I of the present invention are the following:
(2-methyl-4-{methyl-[4-methyl-2-(4-trifluoromethyl-phenyl)-thiazol-5-ylmethyl]-amino}-phenoxy)-acetic acid,
(2-chloro-4-{methyl-[4-methyl-2-(4-trifluoromethyl-phenyl)-thiazol-5-ylmethyl]-amino}-phenoxy)-acetic acid,
(2-fluoro-4-{methyl-[4-methyl-2-(4-trifluoromethyl-phenyl)-thiazol-5-ylmethyl]-amino}-phenoxy)-acetic acid,
(4-{methyl-[4-methyl-2-(4-trifluoromethyl-phenyl)-thiazol-5-ylmethyl]-amino}-2-trifluoromethyl-phenoxy)-acetic acid, and
(2-ethyl-4-{methyl-[4-methyl-2-(4-trifluoromethyl-phenyl)-thiazol-5-ylmethyl]-amino}-phenoxy)-acetic acid.

Also particularly preferred are (2-(3-methoxy-propyl)-4-{methyl-[4-methyl-2-(4-trifluoromethyl-phenyl)-thiazol-5-ylmethyl]-amino}-phenoxy)-acetic acid and (2-methyl-4-{[4-methyl-2-(4-trifluoromethyl-phenyl)-thiazol-5-ylmethyl]-amino}-phenoxy)-acetic acid.

Furthermore, the pharmaceutically acceptable salts of the compounds of formula I and the pharmaceutically acceptable esters of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

As described above, the compounds of formula (I) of the present invention can be used as medicaments for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases (such as e.g. Crohn's disease, inflammatory bowel disease, colitis, pancreatitis, cholestasis/fibrosis of the liver, rheumatoid arthritis, osteoarthritis, psoriasis and other skin disorders, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The compounds can also be used as medicaments for the treatment and/or prevention of obesity. The use as medicament for the treatment of low HDL cholesterol levels, high LDL cholesterol levels, high triglyceride levels, and the metabolic syndrome (syndrome X) is preferred.

The invention therefore also relates to pharmaceutical compositions comprising a compound as defined above and a pharmaceutically acceptable carrier and/or adjuvant. Further, the invention relates to compounds as defined above for use as therapeutically active substances, particularly as therapeutically active substances for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In another embodiment, the invention relates to a method for the treatment and/or prevention of diseases which are modulated by PPARδ and/or PPARα agonists, which method comprises administering a compound of formula (I) to a human or animal. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

The invention further relates to the use of compounds as defined above for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome, obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In addition, the invention relates to the use of compounds as defined above for the preparation of medicaments for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome, obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases. Such medicaments comprise a compound as defined above.

A further aspect of the present invention is the process for the manufacture of compounds of formula (I) as defined above, which process comprises reacting a compound of formula

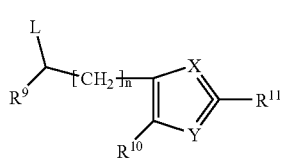

wherein L is a leaving group and X, Y, $R^9$, $R^{10}$, $R^{11}$ and n are as defined as herein before, with an aniline derivative of formula

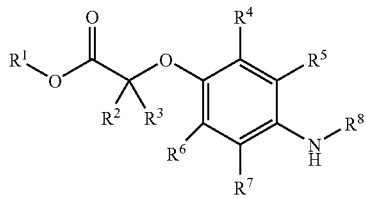

wherein $R^1$ is $C_{1-7}$-alkyl and $R^2$ to $R^8$ are as defined herein before, to obtain a compound of formula

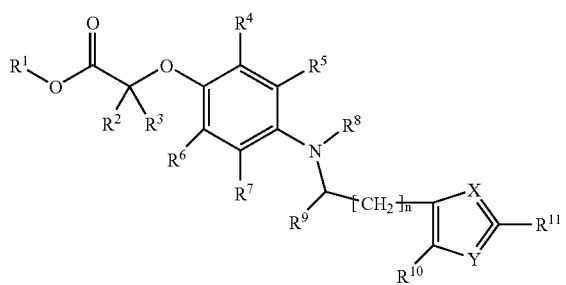

wherein $R^1$ is $C_{1-7}$-alkyl, and optionally hydrolyzing the ester group to obtain a compound of formula I, wherein $R^1$ is hydrogen.

Possible leaving groups L are e.g. methanesulfonate, triflate, chloride or bromide.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

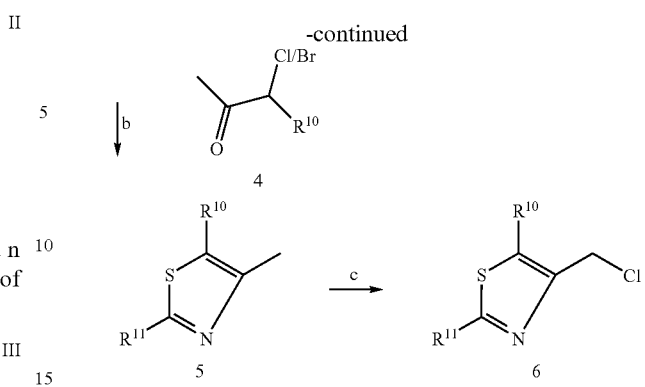

Thioamides 1 of scheme 1 are known or can be prepared by methods known in the art, e.g. by treatment of the corresponding carboxamide with phosphorus pentasulfide or with Lawesson's Reagent [2,4-bis(4-methoxyphenyl)-1,3-dithia-2,4-diphosphetane-2,4-disulfide] in a solvent like toluene at temperatures preferably between 60° C. and the reflux temperature of the solvent. Thioamides 1 of scheme 1 may be condensed with 1,3-dichloroacetone in solvents like acetone or acetonitrile between room temperature and the reflux temperature of the solvents, followed by treatment with strong acid, e.g. concentrated sulfuric acid, preferably at ambient temperature (step a). Alternatively, thioamides 1 of scheme 1 are condensed with alpha-bromo or alpha-chloro ketones 4 of scheme 1 in a solvent like ethanol, preferably at reflux temperature, to give aryl-thiazoles 5 of scheme 1 bearing a methyl function at position 4 (step b) [compare Eur. Pat. Appl. (1987), EP 207453 A2]. By treatment of these aryl-thiazoles 5 of scheme 1 with N-chlorosuccinimide in solvents like acetonitrile, preferably at reflux temperature, chloromethyl compounds 6 of scheme 1 are obtained (step c) [compare PCT Int. Appl. (2001), WO 0119805 A1].

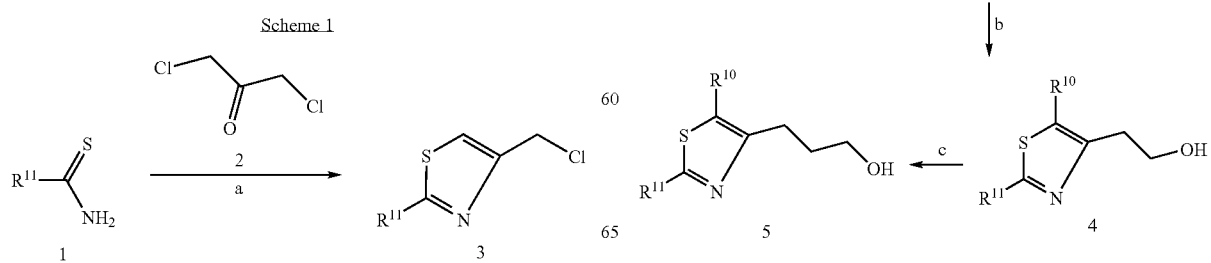

Condensation of thioamides 1 of scheme 2 with a suitable bis-electrophile, e.g. methyl 4-bromo- or 4-chloro-3-oxo-alkanoate 2 of scheme 2, preferably in a solvent like toluene at elevated temperatures (e.g. at reflux temperature), produces thiazoles 3 of scheme 2 carrying an acetic acid ester function at position 4 (step a) [compare PCT Int. Appl. (1997), WO97/31907 A1]. 4-Bromo-3-oxo-alkanoates 2 of scheme 2 are known or can be prepared by methods known in the art [compare PCT Int. Appl. (2001), WO 01/79202 A1]. Thiazoles 3 of scheme 2 can then be reduced, e.g. with lithium aluminum hydride, to alcohols 4 of scheme 2 (step b). Optionally, an elongation of the side chain can then be performed by standard methods, such as transformation of the alcohol into a leaving group, e.g. a mesylate, ensuing treatment with cyanide, saponification and reduction, affording thiazoles 5 of scheme 2 with a hydroxy-propyl function attached to position 4 (step c). Finally, alcohols 4 or 5 of scheme 2 can be converted into compounds of formula 11 of scheme 9, e.g by treatment with methanesulfonyl chloride in dichloromethane in the presence of a base like triethylamine preferably in a temperature range between −20° C. and room temperature or by reaction with carbon tetrachloride or carbon tetrabromide and triphenylphosphine in solvents like tetrahydrofuran preferably in a temperature range between room temperature and the reflux temperature of the solvents; thus yielding compounds of formula 11 of scheme 9 ($R^9$=H) as methanesulfonates, chlorides or bromides, respectively.

Thioamides 1 of scheme 3 can be reacted with 2-halo-acetoacetates 2 of scheme 3 in solvents like ethanol, preferably at reflux temperature, to give thiazole-carboxylic esters 3 (step a). 2-Halo-acetoacetates 2 are known or can be prepared by methods known in the art [compare PCT Int. Appl. (2002), WO 02/062774 A1]. Reduction of the esters 3 of scheme 3, preferably using lithium aluminum hydride in a solvent like ether or tetrahydrofuran, preferably between 0° C. and room temperature, gives primary alohols 4 (step b), which can be used as such or can be converted into the corresponding halides 5, e.g. by treatment with methanesulfonyl chloride in dichloromethane in the presence of 2,6-lutidine, preferably between −20° C. and the reflux temperature of dichloromethane [compare PCT Int. Appl. (2002), WO 02/28433], by treatment with thionyl chloride in a solvent like dichloromethane or chloroform preferably at temperatures between −20° C. and +50° C., or by treatment with tetrabromomethane and triphenylphosphine in solvents like tetrahydrofuran at temperatures between 0° C. and the reflux temperature of tetrahydrofuran (step c). Primary alcohols 4 of scheme 3 can be oxidized to aldehydes 6 by methods known in the art, e.g. by treatment with pyridinium chlorochromate in dichloromethane, preferably at temperatures between room temperature and the reflux temperature of dichloromethane or by treatment with manganese dioxide in solvents like dichloromethane, preferably at room temperature (step d). These aldehydes 6 of scheme 3 can then be converted to the corresponding secondary alcohols 7 through reaction with alkyl organometallic compounds, preferably using alkyl Grignard compounds in a solvent like

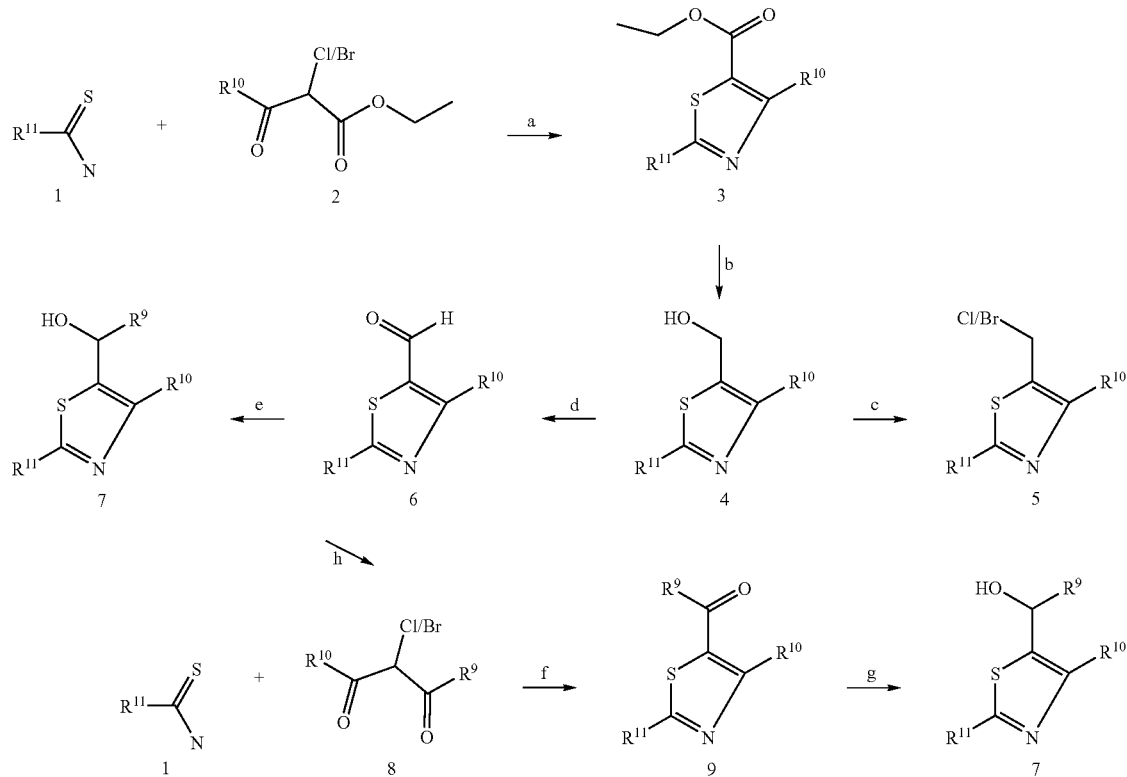

Scheme 3 tetrahydrofuran or ether, preferably between −15° C. and the reflux temperature of the solvent [compare PCT Int. Appl. (2002), WO 02/062774 A1] (step e).

Reaction of thioamides 1 of scheme 3 with 2-halo-1,3-diketones 8 in solvents like ethanol, preferably at reflux temperature, generates thiazole ketones 9 (step f). Alternatively, ketones 9 of scheme 3 can be obtained from secondary alcohols 7 by methods known in the art, e.g. by treatment with Cr(VI) reagents like Jones reagent (Jones et al., *J. Chem. Soc.* 1953, 2548) (step h). These ketones 9 can then be reduced to the corresponding secondary alcohols 7 by methods known in the art, e.g. by treatment with sodium borohydride in alcohol, preferably at temperatures between −15° C. and 40° C. (step g). This reaction can also be carried out in an enantioselective fashion leading to the (R)- or (S)-alcohols 7 of scheme 3, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature according to Corey et al. (E. J. Corey, R. K. Bakshi, S. Shibata, *J. Am. Chem. Soc.* 1987, 109, 5551-5553), or by treatment with (+)- or (−)-B-chlorodiisopinocampheylborane (DIP—Cl), according to Brown et al. (P. V. Ramachandran, B. Gong, A. V. Teodorovic, H. C. Brown, *Tetrahedron: Asymmetry* 1994, 5, 1061-1074). The alcohols 4 and 7 of scheme 3 correspond to or can be converted into compounds of general formula 11 of scheme 9 (n=0), e.g by treatment with methanesulfonyl chloride in dichloromethane in the presence of a base like triethylamine preferably in a temperature range between −20° C. and room temperature, or e.g. by reaction with carbon tetrachloride or carbon tetrabromide and triphenylphosphine in solvents like tetrahydrofuran preferably in a temperature range between room temperature and the reflux temperature of the solvents.

Aryl-thiazole alkanols 1 of scheme 4 comprising a chain length of n carbon atoms can be converted into analogues with a chain length of n+1 carbon atoms by methods well known in the art, e.g. by conversion of the primary alcohol into a suitable leaving group, e.g. a halide (step a), reaction with cyanide (step b), saponification (step c) followed by reduction of the acid formed (compounds 4 of scheme 4) to the primary alcohols 5 ($R^9$=H), e.g. by using diborane in tetrahydrofuran (step d). In order to introduce substituents $R^9$ different from hydrogen, cyano intermediates 3 can be reacted with alkyl Grignard reagents $R^9$MgX in solvents like ether or tetrahydrofuran between 0° C. and the reflux temperature of the solvent to form the corresponding $R^9$CO—alkyl ketones which can be reduced to the corresponding secondary alcohols 5 of scheme 4 by methods known in the art, e.g. by treatment with sodium borohydride in alcohol, preferably at temperatures between −15° C. and 40° C. (step e). This reaction can also be carried out in an enantioselective fashion leading to the (R)- or (S)-alcohols 5 of scheme 4, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature, according to Corey et al. (E. J. Corey, R. K. Bakshi, S. Shibata, *J. Am. Chem. Soc.* 1987, 109, 5551-5553), or by treatment with (+)- or (−)-B-chlorodiisopinocampheyl-borane (DIP—Cl), according to Brown et al. (P. V. Ramachandran, B. Gong, A. V. Teodorovic, H. C. Brown, *Tetrahedron: Asymmetry* 1994, 5, 1061-1074). Primary alcohols 1 of scheme 4 can be oxidized to aldehydes by methods known in the art, e.g. by treatment with pyridinium chlorochromate in dichloromethane, preferably at temperatures between room temperature and the reflux temperature of dichloromethane or by treatment with manganese dioxide in solvents like dichlo-

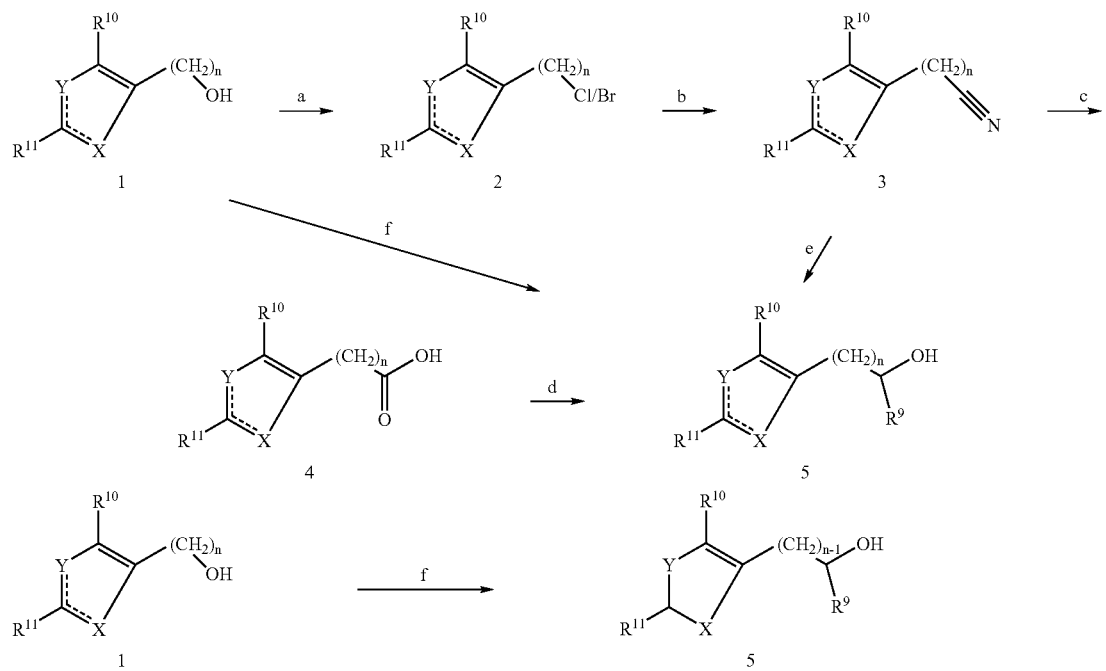

Scheme 4 romethane, preferably at room temperature. These aldehydes can then be converted to the corresponding secondary alcohols 5 through reaction known in the art, e.g. with alkyl organometallic compounds, preferably using alkyl Grignard compounds in a solvent like tetrahydrofuran or ether, preferably between −15° C. and the reflux temperature of the solvent [compare PCT Int. Appl. (2002), WO 02/062774 A1] (step f). Finally, the alcohols 5 of scheme 4 can be converted into compounds of formula 11 of scheme 9, e.g by treatment with methanesulfonyl chloride in dichloromethane in the presence of a base like triethylamine preferably in a temperature range between −20° C. and room temperature or by reaction with carbon tetrachloride or carbon tetrabromide and triphenylphosphine in solvents like tetrahydrofuran preferably in a temperature range between room temperature and the reflux temperature of the solvents; thus yielding compounds of formula 11 of scheme 9 as methanesulfonates, chlorides or bromides, respectively.

Scheme 5

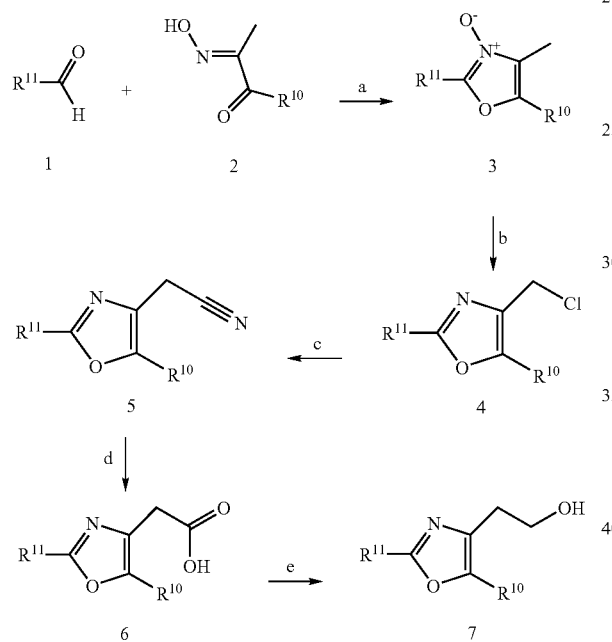

Aldehydes 1 of scheme 5 are commercially available or known. They are condensed with diketo-monoximes 2 of scheme 5 according to literature precedence (Diels, O., Riley, K., Chem. Ber. 1915, 48, 897) in the presence of a strong acid, typically HCl, in a polar solvent like AcOH to yield the oxazole-N-oxides 3 (step a). Subsequent treatment with POCl$_3$ in dichloromethane under reflux provides the corresponding primary chlorides 4 of scheme 5 (Goto, Y., Yamazaki, M., Hamana, M., Chem. Pharm. Bull. 1971, 19, 2050, step b). These intermediates are either used as such, transformed according to well established methods into the corresponding alcohols or activated alcohols like mesylates or tosylates or into the bromides or iodides, or, finally, further elaborated via S$_N$2-reaction with NaCN to give, via nitrites 5 (step c), exhaustive hydrolysis (step d) and reduction (step e), e.g. with borane in tetrahydrofuran, the building blocks 7 of scheme 5.

4-Chloromethyl-2-aryl or 2-heteroaryl-oxazoles 4 of scheme 5 with R$^{10}$ equal hydrogen are preferably prepared from the corresponding aryl or heteroaryl carboxamides and 1,3-dichloroacetone as described e.g. in Bioorg. Med. Chem. Lett. 2000, 10(17), 2041-2044. Finally, the alcohols 7 of scheme 5 can be converted into compounds of formula 11 of scheme 9 (n=1, R$^9$=H), e.g by treatment with methanesulfonyl chloride in dichloromethane in the presence of a base like triethylamine, preferably in a temperature range between −20° C. and room temperature, or by reaction with carbon tetrachloride or carbon tetrabromide and triphenylphosphine in solvents like tetrahydrofuran preferably in a temperature range between room temperature and the reflux temperature of the solvents; thus yielding compounds of formula 11 of scheme 9 as methanesulfonates, chlorides or bromides, respectively.

Scheme 6

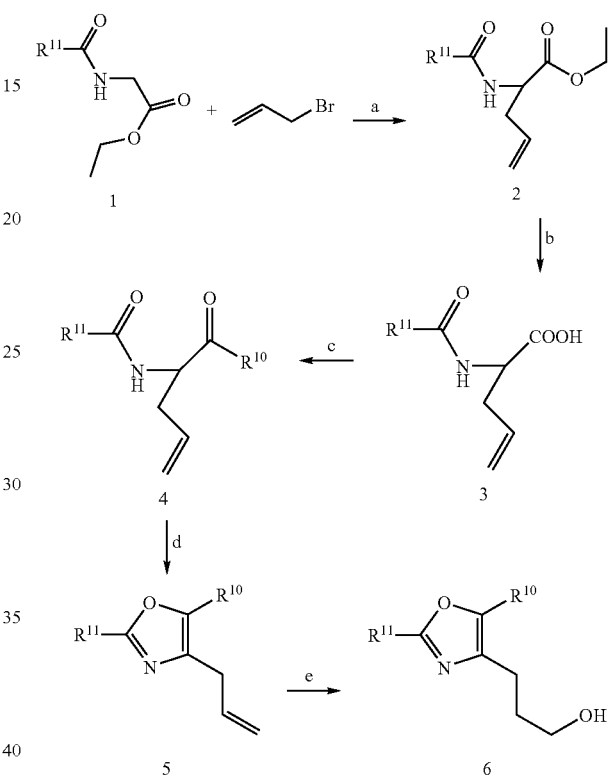

N-Acyl-glycine esters 1 of scheme 6 are either commercially available, known, or can be prepared by standard operations of N-acylation. Mono-allylated esters 2 of scheme 6 can easily be obtained by double deprotonation of 1 with a strong, non-nucleophilic base like LiHMDS in an aprotic solvent like THF, typically at −78° C., followed by treatment with allyl bromide to produce selectively the C-alkylated products 2 (step a). Standard hydrolysis generates intermediate acids 3 (step b), which are then transformed, following well established literature precedence (J. Med. Chem. 1996, 39, 3897), into compounds 4 of scheme 6 (step c). Ring-closure to the oxazole using trifluoro-acetic acid and trifluoro-acetic anhydride as reagents generates key intermediates 5 (step d), which, finally, are elaborated via hydroboration to the target alcohols 6 of scheme 6, e.g. with 9-BBN in THF and ensuing oxidative work-up with H$_2$O$_2$ and NaOH (step e).

Finally, the alcohols 6 of scheme 6 can be converted into compounds of formula 11 of scheme 9 (n=2, R$^9$=H), e.g by treatment with methanesulfonyl chloride in dichloromethane in the presence of a base like triethylamine, preferably in a temperature range between −20° C. and room temperature, or by reaction with carbon tetrachloride or carbon tetrabromide and triphenylphosphine in solvents like tetrahydrofuran, preferably in a temperature range between room temperature and the reflux temperature of the solvents; thus yielding compounds of formula 11 of scheme 9 as methanesulfonates, chlorides or bromides, respectively.

Intermediates of formula 11 of scheme 9 wherein X is oxygen and Y is nitrogen and n is 1 can be obtained e.g. according to scheme 7.

Scheme 7

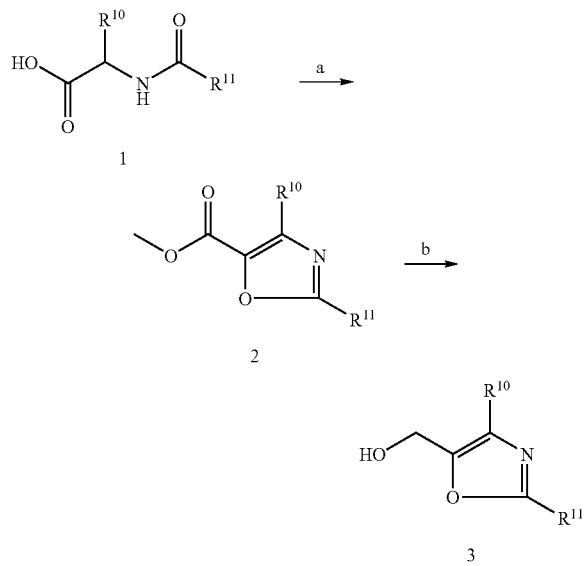

4-Substituted 2-aryloxazol-5-carboxylates 2 ($R^{10}$ equal an alkyl group) can be obtained from N-aroyl-amino acids 1 of scheme 7 as described in (*J. Chem. Soc. Chem. Commun.* 1995, 2335-2336): i) they are treated with oxalyl chloride in solvents like benzene, dichloromethane or tetrahydrofuran, preferably at room temperature, followed by careful evaporation of the solvents after addition of toluene; ii) the thus obtained crude cyclized acid chloride intermediates are treated with triethylamine and methanol (or another alcohol), preferably between 0° C. and room temperature (step a, scheme 7). Reduction of the ester function in compounds 2 of scheme 7 by well known methods e.g. with diisobutyl aluminum hydride in a solvent like tetrahydrofuran, produces primary alcohols 7.3 (step b). Finally, these alcohols 3 of scheme 7 can be converted into compounds of formula 11 of scheme 9 (n=O, $R^9$=H), e.g by treatment with methanesulfonyl chloride in dichloromethane in the presence of a base like triethylamine, preferably in a temperature range between −20° C. and room temperature, or by reaction with carbon tetrachloride or carbon tetrabromide and triphenylphosphine in solvents like tetrahydrofuran, preferably in a temperature range between room temperature and the reflux temperature of the solvents; thus yielding compounds of formula 11 of scheme 9 as methanesulfonates, chlorides or bromides, respectively.

The synthesis of final compounds with the general structure I is described in scheme 8 and scheme 9.

Scheme 8

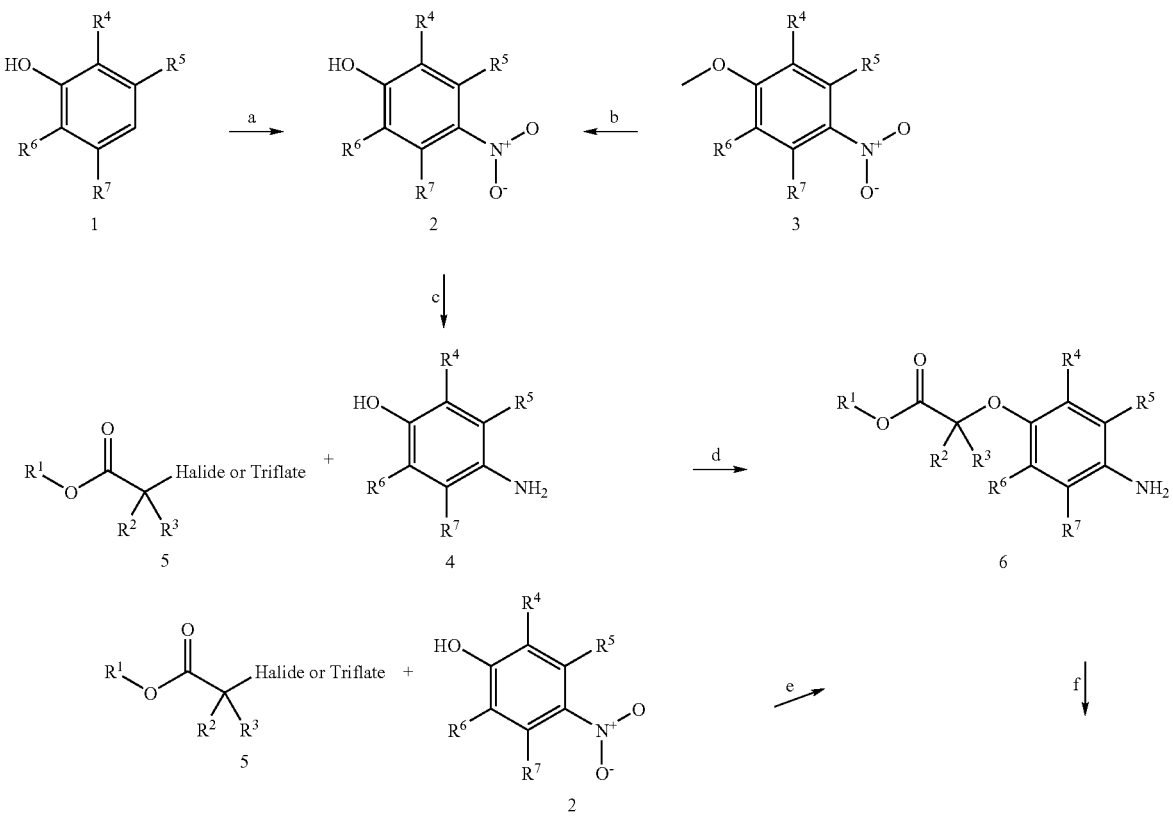

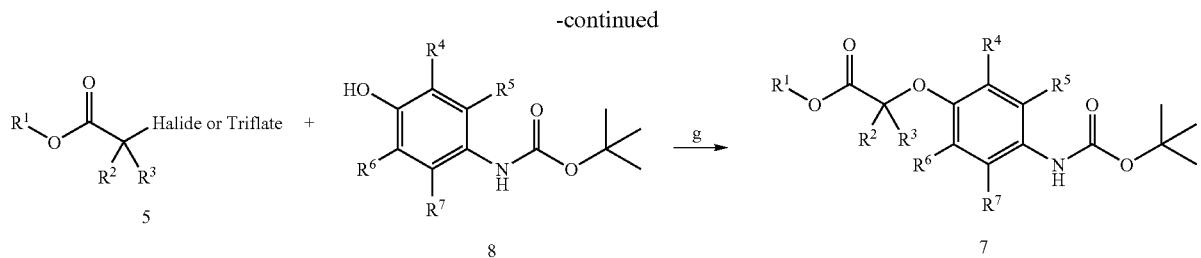

Nitro-phenols 2 of scheme 8 are commercial available or can be synthesized from phenols of the general structure 1, which can be nitrated in para-position according to well established methods, e.g. with a solution of NaNO₃ in water/concentrated hydrochloric acid in a solvent like Et₂O, followed by the addition of acetic acid anhydride at RT [following a procedure of P. Keller, *Bull. Soc. Fr.* 1994, 131, 27-29] (step a). Phenol 2 of scheme 8 can alternatively also be synthesized from anisol 3 by deprotection with aqueous 62% HBr in acetic acid between RT and 120° C. (step b). Nitro-phenol 2 is then hydrogenated in an alcohol like EtOH or MeOH with hydrogen in the presence of Pd/C and an acid like HCl or AcOH at RT to give aniline 4 (step c). Intermediate 4 is then alkylated at oxygen with an acetate, like bromoacetate 5, in the presence of K₂CO₃ or Cs₂CO₃ in a solvent like acetonitrile or acetone between 10° C. and RT to give intermediate 6 of scheme 8 (step d). Halo-acetate 5 is commercial available or can be synthesized by methods known in the art. Triflate 5 can be prepared from the corresponding alcohol. Aniline 6 can also be synthesized from acetate 5 and nitrophenol 2 in a two step procedure: first by O-alkylation as described above, followed by hydrogenation with Pd/C in an alcohol like MeOH or EtOH in the presence of AcOH or HCl (step e). BOC-protection with di-tert-butyl dicarbonate in THF at RT to reflux yields compound 7 of scheme 8 (step f). Alternatively, 7 can also be synthesized directly from bromoacetate 5 and BOC-protected aniline 8 with K₂CO₃ or Cs₂CO₃ as described for the synthesis of 6 (step g).

Scheme 9

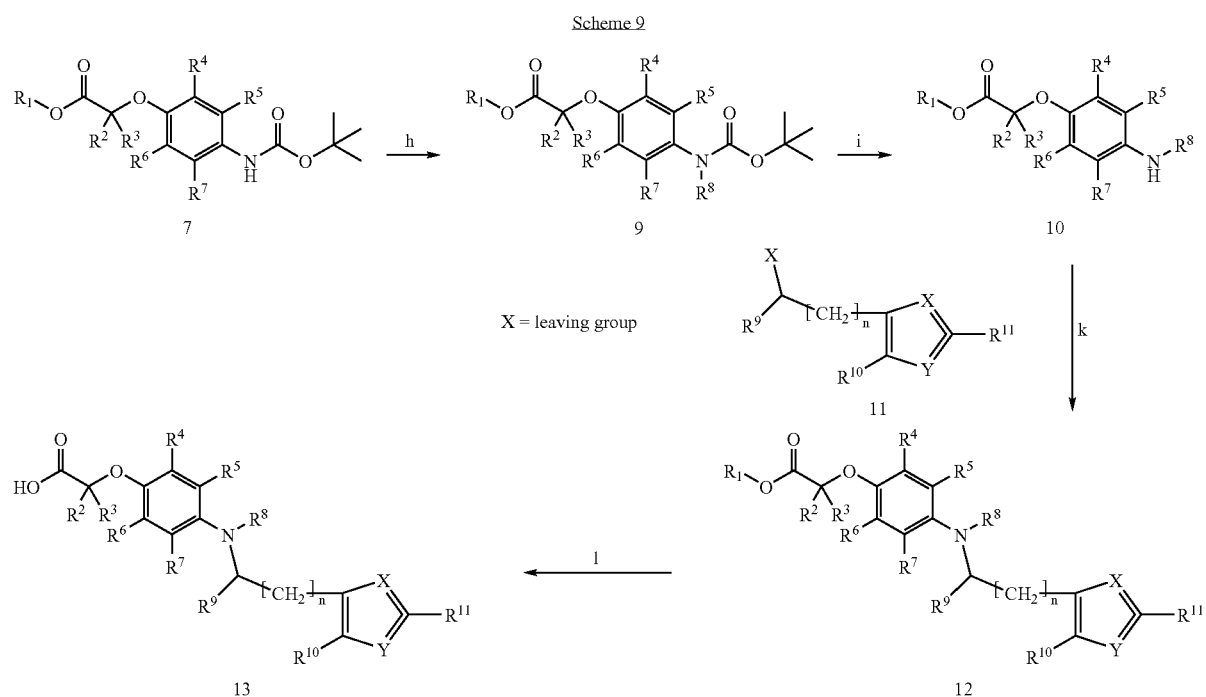

Intermediate 7 of scheme 9 is optionally alkylated at nitrogen using sodium hydride and a reactive alkyl halogenide/mesylate or triflate to give 9 (step h, scheme 9). Standard BOC-deprotection (TFA/CH₂Cl₂, or HCl in dioxane) at 0° C. to RT affords aniline 10 of scheme 9 (step i). Reaction with intermediate 11 using sodium hydride in DMF, DMA or THF, at 0° C. to RT, gave 12 (step k). Alternatively 11 (X=OH) can be transformed with in situ to the corresponding triflate by treatment with trifluoromethanesulfonic anhydride/2,6-di-tert-butylpyridine in CH₂Cl₂ at 0° C. This triflate is then reacted with aniline 10 in the presence of 2,6-di-tert-butylpyridine as base in nitromethane between RT and 60° C. to yield 12 [following a procedure of Belostotskii, Anatoly M., Hassner, A., *Tetrahedron Lett.* 1994, 35(28), 5075-6] (step k). Secondary aniline 12 (R⁸=H) can reductively be methylated with an aqueous solution of NaH₂PO₃ and formaldehyde between RT and 65° C. [Loibner, H., Pruckner, A., Stuetz, A.,

*Tetrahedron Lett.* 1984, 25, 2535-2536]. Ensuing hydrolysis with aqueous LiOH, NaOH or KOH in THF/EtOH or another suitable solvent produces the final acid 13 of scheme 9 (step 1).

The compounds of Formula I, as well as their pharmaceutically acceptable salts possess valuable pharmacological properties. It has been found that they are PPAR activators which leads to their usefulness as lipid modulators and insulin sensitizers. Therefore these compounds are for the treatment of diseases such as diabetes and dyslipidemia. Consequently a further embodiment of the present invention is the use of a compound of Formula I for the treatment of diabetes and dyslipidemia. Yet another embodiment is the use of a compound of Formula I for the manufacture of corresponding medicaments for the treatment of diabetes and dyslipidemia.

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257: 112-119.

Full-length cDNA clones for humans PPARδ and PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARδ (aa 139 to 442), PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assay

PPARδ receptor binding was assayed in HNM10 (50 mM Hepes, pH 7.4, 10 mM NaCl, 5 mM $MgCl_2$, 0.15 mg/ml fatty acid-free BSA and 15 mM DTT). For each 96 well reaction a 500 ng equivalent of GST-PPARδ-LBD fusion protein and radioligand, e.g. 20000 dpm {2-methyl-4-[4-methyl-2-(4-trifluoromethyl-phenyl)-thiazol-5-yl-ditritiom-ethylsulfanyl]-phenoxy}-acetic acid, was bound to 10 µg SPA beads (PharmaciaAmersham) in a final volume of 50 µl by shaking. The resulting slurry was incubated for 1 h at RT and centrifuged for 2 min at 1300 g. The supernatant containing unbound protein was removed and the semidry pellet containing the receptor-coated beads was resuspended in 50 ul of HNM. Radioligand was added and the reaction incubated at RT for 1 h and scintillation proximity counting performed in the presence of test compounds was determined. All binding assays were performed in 96 well plates and the amount of bound ligand was measured on a Packard TopCount using OptiPlates (Packard). Dose response curves were done in triplicates within a range of concentration from $10^{-10}$ M to $10^{-4}$ M.

PPARα receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARα-LBD fusion protein was bound to 10 µg SPA beads (PharmaciaAmersham) in a final volume of 50 µl by shaking. The resulting slurry was incubated for 1 h at RT and centrifuged for 2 min at 1300 g. The supernatant containing unbound protein was removed and the semidry pellet containing the receptor-coated beads was resolved in 50 µl of TKE. For radioligand binding e.g. 10000 dpm of 2(S)-(2-benzoyl-phenylamino)-3-{4-[1,1-d] tritio-2-(5-methyl-2-phenyl-oxazol-4-yl)-ethoxy]-phenyl}-propionic acid or 2,3-ditritio-2(S)-methoxy-3-{4-[2-(5-methyl-2-phenyl-oxazol-4-yl)-ethoxy]-benzo[b]thiophen-7-yl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 µg SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containing the receptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 µl were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% O2:5% $CO_2$ atmosphere. Cells were seeded in 6 well plates at a density of $10^5$ Cells/well and then batch-transfected with either the pFA-PPARδ-LBD, pFA-PPARγ-LBD or pFA-PPARα-LBD expression plasmids plus a reporter plasmid. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final DMSO concentration: 0.1%). Following incubation of the cells for 24 hours with substances, 50 µl of the supernatant was discarded and then 50 µl of Luciferase Constant-Light Reagent (Roche Molecular Biochemicals) to lyse the cells and initiate the luciferase reaction was added. Luminescence for luciferase was measured in a Packard TopCount. Transcriptional activation in the presence of a test substance was expressed as fold-activation over cells incubated in the absence of the substance. EC50 values were calculated using the XLfit program (ID Business Solutions Ltd. UK).

The free acids of the compounds of the present invention ($R^1$ is hydrogen) exhibit $IC_{50}$ values of 0.1 nM to 10 µM, preferably 1 nM to 100 nM for PPARδ and $IC_{50}$ values of 10 nM to 10 µM, preferably 100 nM to 5 µM for PPARα. In addition, the compounds exhibit selectivity of PPARδ/

PPARα of more than 100. Compounds, in which $R^1$ is not hydrogen are converted in vivo to compounds in which $R^1$ is hydrogen. The following table shows measured values for some selected compounds of the present invention.

|  | PPARα $IC_{50}$ (μmol/l) | PPARγ $IC_{50}$ (μmol/l) | PPARδ $IC_{50}$ (μmol/l) |
|---|---|---|---|
| Example 1.6 | 1.75 | >10 | 0.0177 |
| Example 4.6 | 0.412 | >10 | 0.021 |
| Example 5.7 | 1.06 | >10 | 0.0498 |
| Example 6.8 | 0.463 | >10 | 0.0162 |
| Example 7.8 | 0.308 | 2.21 | 0.0101 |
| Example 13.10 | 3.96 | >10 | 0.034 |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Abbreviations:
BOC=t-butyloxycarbonyl, $CH_2Cl_2$=dichloromethane, $CH_3I$=methyl iodide, DMA=dimethylacetamide, DMF=dimethylformamide, EtOAc=ethylacetate, EtOH=ethanol, $Et_2O$=diethylether, $Et_3N$=triethylamine, eq=equivalents, LAH=lithium aluminium hydride, MeOH=methanol, NaH=sodium hydride, $NaBH_4$=sodium borohydride, NaI=sodium iodide, NaCl=sodium chloride, THF=tetrahydrofurane. General remark: All reactions were performed under argon.

Example 1

1.1) (4-Amino-2-methyl-phenoxy)-acetic acid ethyl ester

A solution of ethyl bromoacetate (7.19 ml, 63 mmol) and 4-amino-o-cresol (7.39 g, 60 mmol) in dry acetonitrile (420 ml) was treated at 15° C. with $Cs_2CO_3$ (42.03 g, 129 mmol) and stirred at RT for 2 h. Additional ethyl bromoacetate (0.33 ml, 3 mmol) was added and after 4 h, the mixture was filtered, washed with acetonitrile and evaporated. The residue was suspended in $CH_2Cl_2$, filtered and evaporated to give 13.34 g (quantitative) of (4-amino-2-methyl-phenoxy)-acetic acid ethyl ester as a green oil, MS: 210 ($MH^+$).

1.2) (4-tert-Butoxycarbonylamino-2-methyl-phenoxy)-acetic acid ethyl ester

A solution of (4-amino-2-methyl-phenoxy)-acetic acid ethyl ester (10.46 g, 50 mmol) in THF (150 ml) was treated with of di-tert-butyl dicarbonate (11.69 g, 52.5 mmol) and heated for 2 h at 80° C. The solution was evaporated and extracted with aqueous 10% $KHSO_4/Et_2O$ (3×). The organic phase was washed with aqueous 10% NaCl, dried over $Na_2SO_4$, evaporated and purified by flash chromatography with a gradient of n-heptane:EtOAc 9:1 to 7:1 to yield 11.02 g (71%) of (4-tert-butoxycarbonylamino-2-methyl-phenoxy)-acetic acid ethyl ester as a light yellow crystalline residue, MS: 308 $(M-H)^-$, MP: 78-81° C., dec.

1.3) [4-(tert-Butoxycarbonyl-methyl-amino)-2-methyl-phenoxy]-acetic acid ethyl ester To an ice-cooled and stirred solution of (4-tert-butoxycarbonylamino-2-methyl-phenoxy)-acetic acid ethyl ester (3.09, 10 mmol) in DMF (30 ml) was added within 10 min NaH (55% in oil, 0.65 g, 15 mmol) and after 1 h, $CH_3I$ (4.98 ml, 80 mmol). The reaction was warmed up over night to RT, neutralized at 0° C. with aqueous 10% $KHSO_4$ and extracted with aqueous 10% $KHSO_4/Et_2O$ (3×). The organic phases were washed with aqueous 10% NaCl, dried ($Na_2SO_4$) and evaporated to give 3.46 g (quantitative) of [4-(tert-butoxycarbonyl-methyl-amino)-2-methyl-phenoxy]-acetic acid ethyl ester containing ca 20% ($^1$H-NMR) of [4-(tert-butoxycarbonyl-methyl-amino)-2-methyl-phenoxy]-acetic acid methyl ester, MS: 323 (M, ethyl ester) and 309 (M, methyl ester).

1.4) (2-Methyl-4-methylamino-phenoxy)-acetic acid ethyl ester

A solution of crude [4-(tert-butoxycarbonyl-methyl-amino)-2-methyl-phenoxy]-acetic acid ethyl ester/[4-(tert-butoxycarbonyl-methyl-amino)-2-methyl-phenoxy]-acetic acid methyl ester (3.42 g containing 3.196 g, 9.88 mmol) in $CH_2Cl_2$ (100 ml) was treated at 0° C. with TFA (38 ml) and stirred at RT for 2.5 h. The reaction was evaporated, treated with chilled aqueous saturated $NaHCO_3$ solution/$Et_2O$ (3×). The organic phases were washed with aqueous 10% NaCl, dried ($Na_2SO_4$) and evaporated to give crude (2-Methyl-4-methylamino-phenoxy)-acetic acid ethyl ester with ca 20% of (2-Methyl-4-methylamino-phenoxy)-acetic acid methyl ester. Purification by flash chromatography with a gradient of n-heptane:EtOAc 95:5 to 2:1 yielded 0.83 g (38%) of (2-methyl-4-methylamino-phenoxy)-acetic acid ethyl ester as an orange oil, MS: 224 ($MH^+$) and 0.44 g (21%) of (2-Methyl-4-methylamino-phenoxy)-acetic acid methyl ester as an orange oil, MS: 210 ($MH^+$).

1.5) (2-Methyl-4-{methyl-[4-methyl-2-(4-trifluoromethyl-phenyl)-thiazol-5-ylmethyl]-amino}-phenoxy)-acetic acid ethyl ester To an ice-cooled and stirred solution of (2-methyl-4-methylamino-phenoxy)-acetic acid ethyl ester (0.357 g, 1.6 mmol), 5-chloromethyl-4-methyl-2-(4-trifluoromethyl-phenyl)-thiazole (0.513 g, 1.76 mmol, WO02/28433) and NaI (0.24 g, 1.6 mmol) in DMF (4.8 ml) was added NaH (55% in oil, 0.105 g, 2.4 mmol). The reaction was stirred at RT for 2¾h, diluted with $Et_2O$ and extracted with aqueous 10% $KHSO_4$/$Et_2O$ (3×). The organic phases were washed with aqueous 10% NaCl, dried ($Na_2SO_4$) and evaporated to give 0.87 g (quantitative) of crude (2-methyl-4-{methyl-[4-methyl-2-(4-trifluoromethyl-phenyl)-thiazol-5-ylmethyl]-amino}-phenoxy)-acetic acid ethyl ester as a yellow solid, MS: 479 ($MH^+$).

1.6) (2-Methyl-4-{methyl-[4-methyl-2-(4-trifluoromethyl-phenyl)-thiazol-5-ylmethyl]-amino}-phenoxy)-acetic acid A solution of crude (2-methyl-4-{methyl-[4-methyl-2-(4-trifluoromethyl-phenyl)-thiazol-5-ylmethyl]-amino}-phenoxy)-acetic acid ethyl ester (0.84 g containing 0.74 g, 1.54 mmol) in THF/EtOH (9.2 ml, 1:1) were treated at 0° C. with 1M LiOH (4.6 ml, 4.6 mmol) for 2 min. After 2 h at RT, the solution was acidified by adding aqueous 10% $KHSO_4$, and the mixture was extracted with $Et_2O$ (3×). The organic phase was washed with aqueous 10% NaCl, dried over $Na_2SO_4$ and evaporated. Crystallization ($CH_2Cl_2$/$Et_2O$) gave 0.57 g (82%) (2-methyl-4-{methyl-[4-methyl-2-(4-trifluoromethyl-phenyl)-thiazol-5-ylmethyl]-amino}-phenoxy)-acetic acid as light yellow powder, MS: 449 $(M-H)^-$, MP: 146-149° C., dec.

Example 2

2.1) 2-(4-Trifluoromethyl-phenyl)-thiazole-5-carboxylic acid ethyl ester

To a solution of NaOEt (21% in EtOH, 215 ml, 584 mmol) were added ethyl formate (46.97 ml, 584 mmol) and then, with cooling (max. 28° C.), chloro acetic acid ethyl ester in $Et_2O$ (200 ml). The mixture was stirred at RT for 20 h and filtered after adding $Et_2O$ (200 ml). The resulting solid was dissolved in EtOH (400 ml) and after addition of 4-(trifluoromethyl)benzene-1-carbothioamide (11.98 g, 58.4 mmol) stirring to reflux was accomplished for 20 h. After filtration, the EtOH was removed under reduced pressure and extracted with $CH_2Cl_2$ (3×)/$H_2O$. The organic phases were washed with $H_2O$, dried ($Na_2SO_4$) and evaporated to give crude compound which was crystallized ($Et_2O$/n-pentane) to give 12.43 g (71%) of 2-(4-trifluoromethyl-phenyl)-thiazole-5-carboxylic acid ethyl ester as off-white crystals, MS: 301 ($M^+$), MP: 98-110° C.

2.2) [2-(4-Trifluoromethyl-phenyl)-thiazol-5-yl]-methanol

To a solution of 2-(4-trifluoromethyl-phenyl)-thiazole-5-carboxylic acid ethyl ester (5.122 g, 17.00 mmol) in THF (85 ml) was added dropwise with cooling (15° C.) LAH (1M in THF, 17.34 ml, 17.34 mmol). The resulting mixture was stirred 30 min at RT and the reaction was quenched at ca 15° C. by the cautious addition of 20 ml saturated aqueous $NH_4Cl$ solution. The precipitate was filtered, washed with THF, evaporated and suspended in $CH_2Cl_2$. $Na_2SO_4$ was added and the organic phase filtered and evaporated to give 4.46 g (quantitative) of [2-(4-trifluoromethyl-phenyl)-thiazol-5-yl]-methanol as a yellow crytalline residue, MS: 259 ($M^+$), MP: 95-98° C., dec.

2.3) 5-Chloromethyl-2-(4-trifluoromethyl-phenyl)-thiazole

To an ice-cooled solution of [2-(4-trifluoromethyl-phenyl)-thiazol-5-yl]-methanol (1.556 g, 6.0 mmol) and $Et_3N$ (1.67 ml, 12.0 mmol) in $CH_2Cl_2$ (14 ml) was slowly added methanesulfonyl chloride (0.75 ml, 9.6 mmol). After 2 h at 0° C. more $Et_3N$ (0.17 ml, 1.2 mmol) and methanesulfonyl chloride (0.07 ml, 0.96 mmol) were added. The reaction was kept for 16 h at 0° C. and 4 h at RT until the reaction was completed by TLC (n-heptane/EtOAc 4:1). The reaction was then partitioned between $Et_2O$ (3×)/aqueous saturated $NaHCO_3$. The organic phases were washed once with aqueous 10% $KHSO_4$. and aqueous 10% NaCl, dried over $Na_2SO_4$ and evaporated to give 1.58 g (95%) of 5-chloromethyl-2-(4-trifluoromethyl-phenyl)-thiazole as a light yellow solid, MS: 277 (M, 1Cl), MP: 55-57° C.

2.4) (2-Methyl-4-{methyl-[2-(4-trifluoromethyl-phenyl)-thiazol-5-ylmethyl]-amino}-phenoxy)-acetic acid Analogously, to example 1.5 and 1.6, (2-methyl-4-{methyl-[2-(4-trifluoromethyl-phenyl)-thiazol-5-ylmethyl]-amino}-phenoxy)-acetic acid was prepared from (2-methyl-4-methylamino-phenoxy)-acetic acid methyl ester and 5-chloromethyl-2-(4-trifluoromethyl-phenyl)-thiazole. Light brown foam, MS: 437 ($MH^+$).

Example 3

3.1) 1-[4-Methyl-2-(4-trifluoromethyl-phenyl)-thiazol-5-yl]-ethanone 4-(Trifluoromethyl)benzene-1-carbothiamide (5.03 g, 24.5 mmol) was dissolved in 30 ml of EtOH and treated with 1.05 eq of 3-chloro-2,4-pentanedione (3.46 g, 25.7 mmol); the mixture was kept at 55-60° C. over night. Reducing the total volume to ~¼ and cooling to 0° C. triggered crystallization. Filtration and washing with a tiny amount of cold EtOH afforded 5.49 g of 1-[4-methyl-2-(4-trifluoromethyl-phenyl)-thiazol-5-yl]-ethanone (79%) as yellow crystals of, MS: 285 (M$^+$), MP: 89-90° C.

3.2) (R,S)-1-[4-Methyl-2-(4-trifluoromethyl-phenyl)-thiazol-5-yl]-ethanol

The above prepared 1-[4-methyl-2-(4-trifluoromethyl-phenyl)-thiazol-5-yl]-ethanone (1.90 g, 6.66 mmol) was treated at 0° C. in 50 ml of EtOH with NaBH$_4$ (0.253 g, 6.69 mmol) and kept for another 30 min at ambient temperature. The bulk of solvent was evaporated, the residue taken up in EtOAc, washed twice with water, and dried over MgSO$_4$. Evaporation of the solvents left 1.92 g of (R,S)-1-[4-methyl-2-(4-trifluoromethyl-phenyl)-thiazol-5-yl]-ethanol (99%) as colorless crystals, MS: 287 (M$^+$).

3.3) (R,S)-5-(1-Chloro-ethyl)-4-methyl-2-(4-trifluoromethyl-phenyl)-thiazole The above prepared (R,S)-1-[4-methyl-2-(4-trifluoromethyl-phenyl)-thiazol-5-yl]-ethanol (0.90 g, 3.13 mmol) was dissolved in 40 ml of CH$_2$Cl$_2$ and treated at 0° C. under Argon with 2 eq of SOCl$_2$ (0.454 ml, 6.26 mmol). After additional 60 min at RT, solvent and excess of reagent were carefully removed by evaporation to leave 0.95 g of pure (R,S)-5-(1-chloro-ethyl)-4-methyl-2-(4-trifluoromethyl-phenyl)-thiazole (99%) as colorless solid, MS: 305 (M$^+$, 1Cl).

3.4) (R, S)-[2-Methyl-4-(methyl-{1-[4-methyl-2-(4-trifluoromethyl-phenyl)-thiazol-5-yl]-ethyl}-amino)-phenoxy]-acetic acid Analogously, to example 1.5 and 1.6, from (2-Methyl-4-methylamino-phenoxy)-acetic acid ethyl ester and (R, S)-5-(1-Chloro-ethyl)-4-methyl-2-(4-trifluoromethyl-phenyl)-thiazole was prepared (R, S)-[2-Methyl-4-(methyl-{1-[4-methyl-2-(4-trifluoromethyl-phenyl)-thiazol-5-yl]-ethyl}-amino)-phenoxy]-acetic acid as a light yellow foam, MS: 463 (M-H)$^-$.

Example 4

4.1) (4-Amino-2-chloro-phenoxy)-acetic acid ethyl ester

Analogously, to example 1.1, from 4-amino-2-chlorophenol and ethylbromoacetate was prepared (4-Amino-2-chloro-phenoxy)-acetic acid ethyl ester as a waxy brown solid, MS: 230 (MH$^+$, 1Cl).

4.2) (4-tert-Butoxycarbonylamino-2-chloro-phenoxy)-acetic acid ethyl ester

Analogously, to example 1.2, from (4-amino-2-chloro-phenoxy)-acetic acid ethyl ester and di-tert-butyl dicarbonate was prepared (4-tert-butoxycarbonylamino-2-chloro-phenoxy)-acetic acid ethyl ester as a light yellow powder, MS: 328 [(M-H)$^-$, 1Cl], MP: 119-120° C.

4.3) [4-(tert-Butoxycarbonyl-methyl-amino)-2-chloro-phenoxy]-acetic acid methyl ester Analogously, to example 1.3 from (4-tert-butoxycarbonylamino-2-chloro-phenoxy)-acetic acid ethyl ester and CH$_3$I was prepared [4-(tert-butoxycarbonyl-methyl-amino)-2-chloro-phenoxy]-acetic acid ethyl ester containing [4-(tert-butoxycarbonyl-methyl-amino)-2-chloro-phenoxy]-acetic acid methyl ester, MS: 344 (MH$^+$, 1Cl) and 330 (MH$^+$, 1Cl).

4.4) (2-Chloro-4-methylamino-phenoxy)-acetic acid ethyl ester

Analogously, to example 1.4, crude [4-(tert-butoxycarbonyl-methyl-amino)-2-chloro-phenoxy]-acetic acid ethyl ester containing [4-(tert-butoxycarbonyl-methyl-amino)-2-chloro-phenoxy]-acetic acid methyl ester was TFA deprotected to give (2-chloro-4-methylamino-phenoxy)-acetic acid ethyl ester containing (2-chloro-4-methylamino-phenoxy)-acetic acid methyl ester, MS: 244 (MH$^+$, 1Cl) and 230 (MH$^+$, 1Cl).

4.5) (2-chloro-4-{methyl-[4-methyl-2-(4-trifluoromethyl-phenyl)-thiazol-5-ylmethyl]-amino}-phenoxy)-acetic acid ethyl ester Analogously, to example 1.5, from crude (2-chloro-4-methylamino-phenoxy)-acetic acid ethyl ester containing (2-chloro-4-methylamino-phenoxy)-acetic acid methyl ester and 5-chloromethyl-4-methyl-2-(4-trifluoromethyl-phenyl)-thiazole (WO02/28433) was prepared (2-chloro-4-{methyl-[4-methyl-2-(4-trifluoromethyl-phenyl)-thiazol-5-ylmethyl]-amino}-phenoxy)-acetic acid ethyl ester containing (2-chloro-4-{methyl-[4-methyl-2-(4-trifluoromethyl-phenyl)-thiazol-5-ylmethyl]-amino}-phenoxy)-acetic acid methyl ester, MS: 499 (MH$^+$, 1Cl) and 485 (MH$^+$, 1Cl).

4.6) (2-Chloro-4-{methyl-[4-methyl-2-(4-trifluoromethyl-phenyl)-thiazol-5-ylmethyl]-amino}-phenoxy)-acetic acid Analogously, to example 1.6, from crude (2-chloro-4-{methyl-[4-methyl-2-(4-trifluoromethyl-phenyl)-thiazol-5-ylmethyl]-amino}-phenoxy)-acetic acid ethyl ester containing (2-chloro-4-{methyl-[4-methyl-2-(4-trifluoromethyl-phenyl)-thiazol-5-ylmethyl]-amino}-phenoxy)-acetic acid methyl ester and LiOH was prepared (2-chloro-4-{methyl-[4-methyl-2-(4-trifluoromethyl-phenyl)-thiazol-5-ylmethyl]-amino}-phenoxy)-acetic acid as a yellow powder, MS: 469 [(M-H)$^-$, 1Cl], MP: 149-150° C., dec.

Example 5

5.1) (2-Fluoro-4-nitro-phenoxy)-acetic acid ethyl ester

Analogously, to example 1.1, from 2-fluoro-4-nitrophenol and ethylbromoacetate was prepared (2-fluoro-4-nitro-phenoxy)-acetic acid ethyl ester as a brown crystallin solid, MS: 243 (M$^+$), 56-59° C., dec.

5.2) (4-Amino-2-fluoro-phenoxy)-acetic acid ethyl ester

A solution of (2-fluoro-4-nitro-phenoxy)-acetic acid ethyl ester (17.0 g, 55.92 mmol) in EtOH (330 ml) and aqueous 1M HCl (55.92 ml, 55.92 mmol) was hydrogenated in the presence of 10% Pd/C (1.7 g) for 2 days. After removal of the catalyst the reaction was evaporated and treated with water/Et$_2$O (3×), the aqueous phase was treated with NaHCO$_3$ and extracted with Et$_2$O (3×). The organic phases were washed with aqueous 10% NaCl, dried (Na$_2$SO$_4$) and evaporated to give 5.39 g (45%) of (4-amino-2-fluoro-phenoxy)-acetic acid ethyl ester as a brown crystallin residue, MS: 213 (M⁺).

5.3) (4-tert-Butoxycarbonylamino-2-fluoro-phenoxy)-acetic acid ethyl ester

Analogously, to example 1.2, from (4-amino-2-fluoro-phenoxy)-acetic acid ethyl ester and di-tert-butyl dicarbonate was prepared (4-tert-butoxycarbonylamino-2-fluoro-phenoxy)-acetic acid ethyl ester as light waxy solid, MS: 331 [(M+NH₄)⁺.

5.4) [4-(tert-Butoxycarbonyl-methyl-amino)-2-fluoro-phenoxy]-acetic acid ethyl ester Analogously, to example 1.3, from (4-tert-butoxycarbonylamino-2-fluoro-phenoxy)-acetic acid ethyl ester and CH₃I was prepared [4-(tert-butoxycarbonyl-methyl-amino)-2-fluoro-phenoxy]-acetic acid ethyl ester containing [4-(tert-butoxycarbonyl-methyl-amino)-2-fluoro-phenoxy]-acetic acid methyl ester as a colorless oil, MS: 327 (M⁺) and 313 (M⁺).

5.5) (2-Fluoro-4-methylamino-phenoxy)-acetic acid ethyl ester

Analogously, to example 1.4, crude [4-(tert-butoxycarbonyl-methyl-amino)-2-fluoro-phenoxy]-acetic acid ethyl ester containing [4-(tert-butoxycarbonyl-methyl-amino)-2-fluoro-phenoxy]-acetic acid methyl ester was deprotected with TFA to give (2-fluoro-4-methylamino-phenoxy)-acetic acid ethyl ester containing (2-fluoro-4-methylamino-phenoxy)-acetic acid methyl ester as an orange oil, MS: 228 (MH⁺) and 214 (MH⁺).

5.6) (2-Fluoro-4-{methyl-[4-methyl-2-(4-trifluoromethyl-phenyl)-thiazol-5-ylmethyl]-amino}-phenoxy)-acetic acid ethyl ester Analogously, to example 1.5, from crude (2-fluoro-4-methylamino-phenoxy)-acetic acid ethyl ester containing (2-fluoro-4-methylamino-phenoxy)-acetic acid methyl ester and 5-chloromethyl-4-methyl-2-(4-trifluoromethyl-phenyl)-thiazole (WO02/28433) was prepared (2-fluoro-4-{methyl-[4-methyl-2-(4-trifluoromethyl-phenyl)-thiazol-5-ylmethyl]-amino}-phenoxy)-acetic acid ethyl ester containing (2-fluoro-4-{methyl-[4-methyl-2-(4-trifluoromethyl-phenyl)-thiazol-5-ylmethyl]-amino}-phenoxy)-acetic acid methyl ester as a viscous orange oil, MS: 483 (MH⁺) and 469 (MH⁺).

5.7) (2-Fluoro-4-{methyl-[4-methyl-2-(4-trifluoromethyl-phenyl)-thiazol-5-ylmethyl]-amino}-phenoxy)-acetic acid Analogously, to example 1.6, from crude (2-fluoro-4-{methyl-[4-methyl-2-(4-trifluoromethyl-phenyl)-thiazol-5-ylmethyl]-amino}-phenoxy)-acetic acid ethyl ester containing (2-fluoro-4-{methyl-[4-methyl-2-(4-trifluoromethyl-phenyl)-thiazol-5-ylmethyl]-amino}-phenoxy)-acetic acid methyl ester and LiOH was prepared (2-fluoro-4-{methyl-[4-methyl-2-(4-trifluoromethyl-phenyl)-thiazol-5-ylmethyl]-amino}-phenoxy)-acetic acid as a yellow solid, MS: 453 (M-H)⁻, MP: 113-114° C.

Example 6

6.1) 4-Nitro-2-trifluoromethyl-phenol

A solution of 6-methoxy-5-nitrobenzotrifluoride (24.73 g, 110.7 mmol) in acetic acid (260 ml) and aqueous HBr solution (62%, 130 ml) was heated to reflux for 96 h, cooled, evaporated and taken up in aqueous saturated NaHCO₃ solution/Et₂O (3×). The organic phases were washed with aqueous 10% NaCl, dried over Na₂SO₄ and evaporated to yield 19.27 g (83%) of 4-nitro-2-trifluoromethyl-phenol as yellow solid, MS: 207 (M⁺), MP: 103-104° C.

6.2) (4-Nitro-2-trifluoromethyl-phenoxy)-acetic acid ethyl ester

Analogously, to example 1.1, from 4-nitro-2-trifluoromethyl-phenol and ethyl bromoacetate was prepared (4-nitro-2-trifluoromethyl-phenoxy)-acetic acid ethyl ester as a white solid, MS: 293 (M⁺), MP: 45-46° C.

6.3) (4-Amino-2-trifluoromethyl-phenoxy)-acetic acid ethyl ester

Analogously, to example 5.2, from (4-nitro-2-trifluoromethyl-phenoxy)-acetic acid ethyl ester was prepared (4-amino-2-trifluoromethyl-phenoxy)-acetic acid ethyl ester as an off-white solid, MS: 264 (MH⁺), MP: 78-80° C.

6.4) (4-tert-Butoxycarbonylamino-2-trifluoromethyl-phenoxy)-acetic acid ethyl ester Analogously, to example 1.2, from (4-amino-2-trifluoromethyl-phenoxy)-acetic acid ethyl ester and di-tert-butyl dicarbonate was prepared (4-tert-butoxycarbonylamino-2-trifluoromethyl-phenoxy)-acetic acid ethyl ester as light solid, MS: 381 (M+NH₄)⁺, MP: 104-105° C.

6.5) [4-(tert-Butoxycarbonyl-methyl-amino)-2-trifluoromethyl-phenoxy]-acetic acid methyl ester Analogously, to example 1.3, from (4-tert-butoxycarbonylamino-2-trifluoromethyl-phenoxy)-acetic acid ethyl ester and CH₃I was prepared [4-(tert-butoxycarbonyl-methyl-amino)-2-trifluoromethyl-phenoxy]-acetic acid ethyl ester containing [4-(tert-butoxycarbonyl-methyl-amino)-2-trifluoromethyl-phenoxy]-acetic acid methyl ester as a light yellow oil, MS: 377 (M⁺) and 363 (M⁺).

6.6) (4-Methylamino-2-trifluoromethyl-phenoxy)-acetic acid ethyl ester

Analogously, to example 1.4, crude [4-(tert-butoxycarbonyl-methyl-amino)-2-trifluoromethyl-phenoxy]-acetic acid ethyl ester containing [4-(tert-Butoxycarbonyl-methyl-amino)-2-trifluoromethyl-phenoxy]-acetic acid methyl ester was deprotected with TFA to give (4-methylamino-2-trifluoromethyl-phenoxy)-acetic acid ethyl ester containing (4-methylamino-2-trifluoromethyl-phenoxy)-acetic acid methyl ester as light yellow waxy solid, MS: 278 (MH⁺) and 264 (MH⁺).

6.7) (4-{Methyl-[4-methyl-2-(4-trifluoromethyl-phenyl)-thiazol-5-ylmethyl]-amino}-2-trifluoromethyl-phenoxy)-acetic acid ethyl ester Analogously, to example 1.5, from crude (4-methylamino-2-trifluoromethyl-phenoxy)-acetic acid ethyl ester containing (4-methylamino-2-trifluoromethyl-phenoxy)-acetic acid methyl ester and 5-chloromethyl-4-methyl-2-(4-trifluoromethyl-phenyl)-thiazole (WO02/28433) was prepared (4-{methyl-[4-methyl-2-(4-trifluoromethyl-phenyl)-thiazol-5-ylmethyl]-amino}-2-trifluoromethyl-phenoxy)-acetic acid ethyl ester containing (4-{methyl-[4-methyl-2-(4-trifluoromethyl-phenyl)-thiazol-5-ylmethyl]-amino}-2-trifluoromethyl-phenoxy)-acetic acid methyl ester as a yellow solid, MS: 533 (MH$^+$) and 519 (MH$^+$).

6.8) (4-{Methyl-[4-methyl-2-(4-trifluoromethyl-phenyl)-thiazol-5-ylmethyl]-amino}-2-trifluoromethyl-phenoxy)-acetic acid Analogously, to example 1.6, from crude (4-{methyl-[4-methyl-2-(4-trifluoromethyl-phenyl)-thiazol-5-ylmethyl]-amino}-2-trifluoromethyl-phenoxy)-acetic acid ethyl ester containing (4-{methyl-[4-methyl-2-(4-trifluoromethyl-phenyl)-thiazol-5-ylmethyl]-amino}-2-trifluoromethyl-phenoxy)-acetic acid methyl ester and LiOH was prepared (4-{methyl-[4-methyl-2-(4-trifluoromethyl-phenyl)-thiazol-5-ylmethyl]-amino}-2-trifluoromethyl-phenoxy)-acetic acid as a yellow solid, MS: 503 (M-H)$^-$, MP: 180-181° C.

Example 7

7.1) 2-Ethyl-6-nitro-phenol

To a stirred solution of NaNO$_3$ (8.5 g, 100 mmol) in water (112 ml) and aqueous HCl (25%, 73 ml) was added a solution of 2-ethylphenol in Et$_2$O (560 ml) followed by acetic acid anhydride (3.4 ml, 36 mmol) [P. Keller, An efficient two-phase nitration of para-substituted phenols: application to the synthesis of key intermediates for ferroelectric liquid crystalline compounds, Bull. Soc. Fr. (1994) 131, 27-29]. The reaction was kept a RT with a water bath. After 16 h at RT, additional NaNO$_3$ (4.25 g, 50 mmol) was added. The reaction was treated after 3 h with water/Et$_2$O (3x). The organic phases were washed with water, dried (Na$_2$SO$_4$) and evaporated. Purification by flash chromatography with a gradient of n-heptane:EtOAc 95:5 to 4:1 yielded 7.27 g (43%) 2-ethyl-6-nitro-phenol as a light red liquid, MS: 167 (M$^+$) and 7.49 g (45%) of 2-ethyl-4-nitro-phenol as an orange solid, MS: 167 (M$^+$).

7.2) 4-Amino-2-ethyl-phenol.HCl

A solution of 2-ethyl-4-nitro-phenol (3.34 g, 20.00 mmol) in MeOH (40 ml) and aqueous 1M HCl (20 ml, 20.00 mmol) was hydrogenated in the presence of 10% Pd/C (0.33 g) for 4 h. After removal of the catalyst the reaction was evaporated and suspended in CH$_2$Cl$_2$ and a small amount of MeOH, dried (Na$_2$SO$_4$) and evaporated to give 3.35 g (96%) of 4-amino-2-ethyl-phenol.HCl, MS: 138 (MH$^+$), MP: 239-240° C., dec.

7.3) (4-Amino-2-ethyl-phenoxy)-acetic acid tert-butyl ester

Analogously, to example 1.1, from 4-amino-2-ethyl-phenol.HCl and ethyl bromoacetate with 3.15 eq of Cs$_2$CO$_3$ was prepared (4-amino-2-ethyl-phenoxy)-acetic acid tert-butyl ester, MS: 252 (MH$^+$).

7.4) (4-tert-Butoxycarbonylamino-2-ethyl-phenoxy)-acetic acid methyl ester

A solution of (4-amino-2-ethyl-phenoxy)-acetic acid tert-butyl ester (0.77 g, 3.06 mmol) in THF (9 ml) was treated with of di-tert-butyl dicarbonate (0.70 g, 3.22 mmol) and heated for 1.5 h at 80° C. Additional di-tert-butyl dicarbonate (0.20 g, 0.92 mmol) were added and heated for 1.5 h at 80° C. The solution was evaporated and extracted with aqueous 10% KHSO$_4$/Et$_2$O (3x). The organic phase was washed with aqueous 10% NaCl, dried over Na$_2$SO$_4$. The residue was dissolved in MeOH (20 ml), treated with Cs$_2$CO$_3$ (0.1 g (0.31 mmol) and after 3 h again with Cs$_2$CO$_3$ (0.9 g (0.2.76 mmol). After 2h at RT, the suspension was kept at 4° C. for 16 h, filtered and evaporated. After extraction with aqueous 10% KHSO$_4$/Et$_2$O (3x), the organic phase was washed with aqueous 10% NaCl, dried over Na$_2$SO$_4$ to yield 1.63 g (quantitative) of (4-tert-butoxycarbonylamino-2-ethyl-phenoxy)-acetic acid methyl ester as a viscous dark brown oil, MS: 309 (M$^+$).

7.5) [4-(tert-Butoxycarbonyl-methyl-amino)-2-ethyl-phenoxy]-acetic acid methyl ester Analogously, to example 1.3 from (4-tert-butoxycarbonylamino-2-ethyl-phenoxy)-acetic acid methyl ester and CH$_3$I was prepared [4-(tert-butoxycarbonyl-methyl-amino)-2-ethyl-phenoxy]-acetic acid methyl ester as a viscous yellow oil, MS: 324 (MH$^+$).

7.6) (2-Ethyl-4-methylamino-phenoxy)-acetic acid methyl ester

Analogously, to example 1.4, [4-(tert-butoxycarbonyl-methyl-amino)-2-ethyl-phenoxy]-acetic acid methyl ester was deprotected with TFA to give (2-ethyl-4-methylamino-phenoxy)-acetic acid methyl ester as a light brown oil, MS: 224 (MH$^+$).

7.7) (2-Ethyl-4-{methyl-[4-methyl-2-(4-trifluoromethyl-phenyl)-thiazol-5-ylmethyl]-amino}-phenoxy)-acetic acid methyl ester Analogously, to example 1.5, from crude (2-ethyl-4-methylamino-phenoxy)-acetic acid methyl ester and 5-chloromethyl-4-methyl-2-(4-trifluoromethyl-phenyl)-thiazole (WO02/28433) was prepared (2-ethyl-4-{methyl-[4-methyl-2-(4-trifluoromethyl-phenyl)-thiazol-5-ylmethyl]-amino}-phenoxy)-acetic acid methyl ester as a yellow viscous oil, MS: 479 (MH$^+$).

7.8) (2-Ethyl-4-{methyl-[4-methyl-2-(4-trifluoromethyl-phenyl)-thiazol-5-ylmethyl]-amino}-phenoxy)-acetic acid Analogously, to example 1.6 from crude (2-ethyl-4-{methyl-[4-methyl-2-(4-trifluoromethyl-phenyl)-thiazol-5-ylmethyl]-amino}-phenoxy)-acetic acid methyl ester and LiOH was prepared (2-ethyl-4-{methyl-[4-methyl-2-(4-trifluoromethyl-phenyl)-thiazol-5-ylmethyl]-amino}-phenoxy)-acetic acid as a light grey solid, MS: 463 (M-H)$^-$, MP: 142-143° C., dec.

Example 8

8.1) (2-Methoxy-4-nitro-phenoxy)-acetic acid ethyl ester

Analogously, to example 1.1, from 4-nitroguaiacol and ethylbromoacetate was prepared (2-methoxy-4-nitro-phenoxy)-acetic acid ethyl ester as a yellow powder, MS: 255 (M$^+$).

8.2) (4-Amino-2-methoxy-phenoxy)-acetic acid ethyl ester

Analogously, to example 7.2, from (2-methoxy-4-nitrophenoxy)-acetic acid ethyl ester was prepared (4-amino-2-methoxy-phenoxy)-acetic acid ethyl ester as a dark brown oil, MS: 284 (M+OAc)⁻.

8.3) (4-tert-Butoxycarbonylamino-2-methoxy-phenoxy)-acetic acid ethyl ester

Analogously, to example 1.2, from (4-amino-2-methoxy-phenoxy)-acetic acid ethyl ester and di-tert-butyl dicarbonate was prepared (4-tert-butoxycarbonylamino-2-methoxy-phenoxy)-acetic acid ethyl ester as light yellow solid, MS: 343 (M+NH$_4$)⁺, MP: 81-83° C.

8.4) [4-(tert-Butoxycarbonyl-methyl-amino)-2-methoxy-phenoxy]-acetic acid ethyl ester Analogously, to example 1.3, from (4-tert-butoxycarbonylamino-2-methoxy-phenoxy)-acetic acid ethyl ester and CH$_3$I was prepared [4-(tert-butoxycarbonyl-methyl-amino)-2-methoxy-phenoxy]-acetic acid ethyl ester containing [4-(tert-butoxycarbonyl-methyl-amino)-2-methoxy-phenoxy]-acetic acid methyl ester as a light brown viscous oil, MS: 339 (M⁺) and 325 (M⁺).

8.5) (2-Methoxy-4-methylamino-phenoxy)-acetic acid ethyl ester

Analogously, to example 1.4, crude [4-(tert-butoxycarbonyl-methyl-amino)-2-methoxy-phenoxy]-acetic acid ethyl ester containing [4-(tert-butoxycarbonyl-methyl-amino)-2-methoxy-phenoxy]-acetic acid methyl ester was deprotected with TFA to give (2-methoxy-4-methylamino-phenoxy)-acetic acid ethyl ester containing (2-methoxy-4-methylamino-phenoxy)-acetic acid methyl ester as a brown oil, MS: 240 (MH⁺) and 226 (MH⁺).

8.6) (2-Methoxy-4-{methyl-[4-methyl-2-(4-trifluoromethyl-phenyl)-thiazol-5-ylmethyl]-amino}-phenoxy)-acetic acid ethyl ester Analogously, to example 1.5, from crude (2-methoxy-4-methylamino-phenoxy)-acetic acid ethyl ester containing (2-methoxy-4-methylamino-phenoxy)-acetic acid methyl ester and 5-chloromethyl-4-methyl-2-(4-trifluoromethyl-phenyl)-thiazole (WO02/28433) was prepared (2-methoxy-4-{methyl-[4-methyl-2-(4-trifluoromethyl-phenyl)-thiazol-5-ylmethyl]-amino}-phenoxy)-acetic acid ethyl ester containing (2-methoxy-4-{methyl-[4-methyl-2-(4-trifluoromethyl-phenyl)-thiazol-5-ylmethyl]-amino}-phenoxy)-acetic acid methyl ester as a light brown semisolid, MS: 495 (MH⁺) and 481 (MH⁺).

8.7) (2-Methoxy-4-{methyl-[4-methyl-2-(4-trifluoromethyl-phenyl)-thiazol-5-ylmethyl]-amino}-phenoxy)-acetic acid Analogously, to example 1.6, from crude (2-methoxy-4-{methyl-[4-methyl-2-(4-trifluoromethyl-phenyl)-thiazol-5-ylmethyl]-amino}-phenoxy)-acetic acid ethyl ester containing (2-methoxy-4-{methyl-[4-methyl-2-(4-trifluoromethyl-phenyl)-thiazol-5-ylmethyl]-amino}-phenoxy)-acetic acid methyl ester and LiOH was prepared (2-methoxy-4-{methyl-[4-methyl-2-(4-trifluoromethyl-phenyl)-thiazol-5-ylmethyl]-amino}-phenoxy)-acetic acid as a light yellow powder, MS: 465 (M-H)⁻, MP: 129-131° C., dec.

Example 9

9.1) (4-tert-Butoxycarbonylamino-phenoxy)-acetic acid ethyl ester

Analogously, to example 1.1, from (4-hydroxy-phenyl)-carbamic acid tert-butyl ester and ethylbromoacetate was prepared (4-tert-butoxycarbonylamino-phenoxy)-acetic acid ethyl ester as an off-white semisolid, MS: 296 (MH⁺).

9.2) [4-(tert-Butoxycarbonyl-ethyl-amino)-phenoxy]-acetic acid ethyl ester

Analogously, to example 1.3 from (4-tert-butoxycarbonylamino-phenoxy)-acetic acid ethyl ester and iodoethane was prepared [4-(tert-butoxycarbonyl-ethyl-amino)-phenoxy]-acetic acid ethyl ester, MS: 324 (MH⁺).

9.3) (4-Ethylamino-phenoxy)-acetic acid ethyl ester

Analogously, to example 1.4, crude [4-(tert-butoxycarbonyl-ethyl-amino)-phenoxy]-acetic acid ethyl ester was deprotected with TFA to give (4-ethylamino-phenoxy)-acetic acid ethyl ester as light brown oil, MS: 224 (MH⁺).

9.4) (4-{Ethyl-[4-methyl-2-(4-trifluoromethyl-phenyl)-thiazol-5-ylmethyl]-amino}-phenoxy)-acetic acid To an ice-cooled and stirred solution of crude (4-ethylamino-phenoxy)-acetic acid ethyl ester (0.243 g, containing 0.214 g, 0.96 mmol), 5-chloromethyl-4-methyl-2-(4-trifluoromethyl-phenyl)-thiazole (0.308 g, 1.05 mmol, WO02/28433) and NaI (0.144 g, 0.96 mmol) in DMF (3 ml) was added NaH (55% in oil, 0.063 g, 1.44 mmol). The reaction was stirred at RT for 4 h, water was added and diluted with Et$_2$O and extracted with aqueous saturated NaHCO$_3$/Et$_2$O (3×). The organic phases were washed with aqueous saturated NaHCO$_3$, dried (Na$_2$SO$_4$) and evaporated to give 0.32 g (70%) of crude (4-{ethyl-[4-methyl-2-(4-trifluoromethyl-phenyl)-thiazol-5-ylmethyl]-amino}-phenoxy)-acetic acid ethyl ester as an orange oil, MS: 479 (MH⁺).

The aqueous phases were combined, acidified with KHSO$_4$ and extracted with Et$_2$O (3×). The organic phase was washed with aqueous 10% NaCl, dried over Na$_2$SO$_4$, evaporated and purified by flash chromatography with a gradient of CH$_2$Cl$_2$:MeOH 99:1 to 95:5 to yield 0.078 g (18%) of (4-{ethyl-[4-methyl-2-(4-trifluoromethyl-phenyl)-thiazol-5-ylmethyl]-amino}-phenoxy)-acetic acid as a light yellow solid, MS: 451 (MH⁺).

Example 10

10.1) (4-{Ethyl-[2-(4-trifluoromethyl-phenyl)-thiazol-5-ylmethyl]-amino}-phenoxy)-acetic acid Analogously, to example 9.4, from (4-ethylamino-phenoxy)-acetic acid ethyl ester and 5-chloromethyl-2-(4-trifluoromethyl-phenyl)-thiazole (as prepared in example 2.3) was prepared (4-{ethyl-[2-(4-trifluoromethyl-phenyl)-thiazol-5-ylmethyl]-amino}-phenoxy)-acetic acid as a light brown foam, MS: 437 (MH⁺).

Example 11

11.1) (4-{tert-Butoxycarbonyl-[4-methyl-2-(4-trifluoromethyl-phenyl)-thiazol-5-ylmethyl]-amino}-phenoxy)-acetic acid ethyl ester To an ice-cooled and stirred solution of (4-tert-butoxycarbonylamino-phenoxy)-acetic acid ethyl ester (0.295, 1 mmol) and 5-chloromethyl-2-(4-trifluoromethyl-phenyl)-thiazole (0.292, 1 mmol) in DMA (10 ml) was added NaH (55% in oil, 0.065 g, 1.5 mmol). The reaction was warmed up and stirred for 5 h at RT, neutralized at 0° C. with aqueous 10% $KHSO_4$ and extracted with aqueous 10% $KHSO_4/Et_2O$ (3×). The organic phases were washed with aqueous 10% NaCl, dried ($Na_2SO_4$) and evaporated. Purification by flash chromatography with a gradient of $CH_2Cl_2$:$Et_2O$ 99:1 to 98:2 yielded 0.207 g (38%) of (4-{tert-butoxycarbonyl-[4-methyl-2-(4-trifluoromethyl-phenyl)-thiazol-5-ylmethyl]-amino}-phenoxy)-acetic acid ethyl ester as a yellow viscous oil, MS: 551 ($MH^+$).

11.2) (4-{[4-Methyl-2-(4-trifluoromethyl-phenyl)-thiazol-5-ylmethyl]-amino}-phenoxy)-acetic acid ethyl ester Analogously, to example 1.4, (4-{tert-butoxycarbonyl-[4-methyl-2-(4-trifluoromethyl-phenyl)-thiazol-5-ylmethyl]-amino}-phenoxy)-acetic acid ethyl ester was deprotected with TFA to give (4-{[4-methyl-2-(4-trifluoromethyl-phenyl)-thiazol-5-ylmethyl]-amino}-phenoxy)-acetic acid ethyl ester, MS: 451 ($MH^+$), MP: 153-155° C., dec.

11.3) (4-{[4-Methyl-2-(4-trifluoromethyl-phenyl)-thiazol-5-ylmethyl]-amino}-phenoxy)-acetic acid Analogously, to example 1.6, from (4-{[4-methyl-2-(4-trifluoromethyl-phenyl)-thiazol-5-ylmethyl]-amino}-phenoxy)-acetic acid ethyl ester, (4-{[4-methyl-2-(4-trifluoromethyl-phenyl)-thiazol-5-ylmethyl]-amino}-phenoxy)-acetic acid was prepared as a light yellow powder, MS: 421 $(M-H)^-$.

Example 12

12.1) (4-{Methyl-[4-methyl-2-(4-trifluoromethyl-phenyl)-thiazol-5-ylmethyl]-amino}-phenoxy)-acetic acid ethyl ester A solution of (4-{[4-methyl-2-(4-trifluoromethyl-phenyl)-thiazol-5-ylmethyl]-amino}-phenoxy)-acetic acid ethyl ester (0.09 g, 0.2 mmol) in dioxane (1 mL) was treated with 1N $NaH_2PO_3$ solution (1 ml) and a 37% aqueous solution of formaldehyde (1 ml). The mixture was heated to 60° C. for 7.5 h. Additional dioxane (1 ml) was added and heated for 11.5 h. The mixture was extracted with aqueous saturated $NaHCO_3$ solution/$Et_2O$ (3×). The organic phases were washed with aqueous 10% NaCl, dried ($Na_2SO_4$) and evaporated to give 0.08 g (86%) of (4-{methyl-[4-methyl-2-(4-trifluoromethyl-phenyl)-thiazol-5-ylmethyl]-amino}-phenoxy)-acetic acid ethyl ester as yellow waxy solid, MS: 465 ($MH^+$).

12.2) (4-{Methyl-[4-methyl-2-(4-trifluoromethyl-phenyl)-thiazol-5-ylmethyl]-amino}-phenoxy)-acetic acid Analogously, to example 1.6, from (4-{methyl-[4-methyl-2-(4-trifluoromethyl-phenyl)-thiazol-5-ylmethyl]-amino}-phenoxy)-acetic acid ethyl ester and LiOH was prepared (4-{methyl-[4-methyl-2-(4-trifluoromethyl-phenyl)-thiazol-5-ylmethyl]-amino}-phenoxy)-acetic acid as a yellow powder, MS: 435 $(M-H)^-$.

Example 13

13.1) (2-Iodo-phenoxy)-acetic acid ethyl ester 9.10 g (41.4 mmol) of o-iodophenol was dissolved in 102 ml of acetone and treated subsequently at 0° C. with 14.8 g (1.1 eq.) of cesium carbonate and 4.57 ml (1.0 eq.) of ethyl bromoacetate. After vigorous stirring for 1 h at ambient temperature and filtration, the bulk of solvent was evaporated and the residue redissolved in EtOAc. Washing with water, drying over magnesium sulfate, and evaporation of the solvents finally produced 12.66 g of pure title compound as colorless oil, MS: 306.0 $(M)^+$.

13.2) [2-(3-Methoxy-prop-1-ynyl)-phenoxy]-acetic acid ethyl ester

A three neck reaction flask was successively charged with 12.65 g (41.3 mmol) of the above prepared (2-iodo-phenoxy)-acetic acid ethyl ester, 128 ml of acetonitrile, 5.793 g (2 eq.) of 3-methoxy-1-propyne, 17.28 ml (3 eq.) of $NEt_3$, 1.45 g (0.05 eq.) of $(PPh_3)_2PdCl_2$, and 0.394 g (0.05 eq.) of CuI. After stirring for 4 h the bulk of the solvent was removed i. V. and the residue distributed between HCl and EtOAc. Washing of the organic layer with cold water and brine, drying over magnesium sulfate, and evaporation of the solvents, followed by flash chromatography ($SiO_2$, hexane/EtOAc=8/2), yielded 9.54 g of the title compound as light brown oil, MS: 248.2 $(M)^+$.

13.3) [2-(3-Methoxy-propyl)-phenoxy]-acetic acid ethyl ester 9.54 g (38.4 mmol) of the above prepared [2-(3-methoxy-prop-1-ynyl)-phenoxy]-acetic acid ethyl ester was hydrogenated at RT in 130 ml of EtOAc over 2.39 g of Pd/C (10%) under 1 atm. of $H_2$-pressure. After 2 h at ambient temperature, the reaction mixture was filtrated over Celite and carefully rinsed with EtOAc. Evaporation of the solvent left finally 9.39 g of the title compound as colorless oil, MS: 252.2 $(M)^+$.

13.4) [2-(3-Methoxy-propyl)-4-nitro-phenoxy]-acetic acid ethyl ester 4.00 g (15.9 mmol) of the above prepared [2-(3-methoxy-propyl)-phenoxy]-acetic acid ethyl ester was dissolved in 5.0 ml of TFAA and added slowly and carefully via dropping funnel to a mixture of 5 ml of TFAA and 4 ml of conc. $HNO_3$ (65%) kept at −10° C.; the reaction was then allowed to proceed for additional 30 min. Careful quenching with ice, twofold extraction with EtOAc, washing with $NaHCO_3$ and brine, drying over magnesium sulfate, and evaporation of the solvents left a crude product which was purified by flash chromatography ($SiO_2$, hexane/EtOAc=75/25) to deliver finally 3.00 g of the title compound as light brown oil, contaminated according to NMR with roughly 35% of the ortho-isomer which was separated after the next step, MS: 298.3 $(MH^+)^+$.

13.5) [4-Amino-2-(3-methoxy-propyl)-phenoxy]-acetic acid ethyl ester 3.00 g (roughly 65%, 6.56 mmol) of the above prepared [2-(3-methoxy-propyl)-4-nitro-phenoxy]-acetic acid ethyl ester was hydrogenated at RT in 50 ml of EtOAc over 0.60 g of Pd/C (10%) under 1 atm. of $H_2$-pressure. After 3 h at ambient temperature, the reaction mixture was filtered over Celite and carefully rinsed with EtOAc. Evaporation of the solvent, followed by flash chromatography ($SiO_2$, hexane/EtOAc=1/1) produced 1.69 g of the title compound as light brown oil; from the more polar fractions, 0.784 g of 8-(3-methoxy-propyl)-4H-benzo[1,4]oxazin-3-one was isolated (cyclized reduced ortho-amino derivative), MS: 268.3 $(MH^+)^+$; side product: 221.1 $(M)^+$.

13.6) [4-tert-Butoxycarbonylamino-2-(3-methoxy-propyl)-phenoxy]-acetic acid ethyl ester 1.68 g (6.28 mmol) of the above prepared [4-amino-2-(3-methoxy-propyl)-phenoxy]-acetic acid ethyl ester was dissolved in 7 ml of THF, treated with 1.646 g (1.2 eq.) of di-tert-butyl dicarbonate, and refluxed for 1 h. After cooling, the reaction mixture was poured onto crashed ice/EtOAc, the organic layer washed with water and brine, dried over magnesium sulfate, and evaporated to dryness. Flash chromatography ($SiO_2$, hexane/EtOAc=75/25) afforded 2.22 g of the title compound as light brown oil, MS: 387.2 $(M)^+$.

13.7) [4-(tert-Butoxycarbonyl-methyl-amino)-2-(3-methoxy-propyl)-phenoxy]-acetic acid ethyl ester To 2.21 g (6.01 mmol) of the above prepared [4-tert-butoxycarbonylamino-2-(3-methoxy-propyl)-phenoxy]-acetic acid ethyl ester, dissolved in 18 ml of abs. DMF, was added at 0° C. 0.313 g of NaH (60% in mineral oil, 1.3 eq.). 5 min later, 0.75 ml (2 eq.) of MeI was added and the reaction allowed to proceed for 10 min at 0° C. and for 1 h at ambient temperature. Pouring onto crashed ice/aqueous 10% $KHSO_4$, twofold extraction with EtOAc, washing with water and brine, drying over magnesium sulfate, and evaporation of the solvents, followed by flash chromatography ($SiO_2$, hexane/EtOAc=8/2), yielded 1.55 g of the title compound as light yellow oil.

13.8) [2-(3-Methoxy-propyl)-4-methylamino-phenoxy]-acetic acid ethyl ester 1.55 g (4.06 mmol) of the above prepared [4-(tert-butoxycarbonyl-methyl-amino)-2-(3-methoxy-propyl)-phenoxy]-acetic acid ethyl ester was dissolved in 41 ml of $CH_2Cl_2$ and treated dropwise with 10 ml of TFA. After additional 30 min at RT, the bulk of the solvents was removed i. V. and the residue distributed between cold $NaHCO_3$-solution and EtOAc. Washing with cold water and brine, drying over magnesium sulfate, and evaporation of the solvents left 1.15 g of the title compound as brownish oil which was used as such for the next step.

13.9) (2-(3-Methoxy-propyl)-4-{methyl-[4-methyl-2-(4-trifluoromethyl-phenyl)-thiazol-5-ylmethyl]-amino}-phenoxy)-acetic acid ethyl ester To 0.216 g (0.77 mmol) of the above prepared [2-(3-methoxy-propyl)-4-methylamino-phenoxy]-acetic acid ethyl ester, dissolved in 2.4 ml of abs. DMF, were added successively at 0° C. 0.037 g of NaH (60% in mineral oil, 1.2 eq.), 0.115 g (1 eq.) of NaI and 0.215 g (0.96 eq.) of 5-chloromethyl-4-methyl-2-(4-trifluoromethyl-phenyl)-thiazole (WO02/28433). The reaction was allowed to proceed for 5 min at 0° C. and for 0.5 h at ambient temperature. Pouring onto crashed ice/aqueous 10% $KHSO_4$, twofold extraction with EtOAc, washing with water and brine, drying over magnesium sulfate, and evaporation of the solvents, followed by flash chromatography ($SiO_2$, hexane/EtOAc=78/22), yielded 0.284 g of the title compound as light yellow oil, MS: 537.5 $(MH)^+$.

13.10) (2-(3-Methoxy-propyl)-4-{methyl-[4-methyl-2-(4-trifluoromethyl-phenyl)-thiazol-5-ylmethyl]-amino}-phenoxy)-acetic acid 0.280 g (0.52 mmol) of the above prepared (2-(3-methoxy-propyl)-4-{methyl-[4-methyl-2-(4-trifluoromethyl-phenyl)-thiazol-5-ylmethyl]-amino}-phenoxy)-acetic acid ethyl ester was dissolved in 3.3 ml of THF/EtOH=1/1, treated with 1.56 ml (3 eq.) of 1N NaOH, and kept at ambient temperature for 0.5 h. The reaction mixture was then poured onto crashed ice/HCl dil., extracted twice with EtOAc, the organic layer washed with water and brine, dried over sodium sulfate, and evaporated to dryness. Crystallization from hexane/EtOAc afforded finally 0.209 g of the title compound as off-white crystals of mp. 142-143° C., MS: 507.5 $(M-H)^-$.

Example 14

(2-Methyl-4-{methyl-[4-methyl-2-(4-trifluoromethyl-phenyl)-oxazol-5-ylmethyl]-amino}-phenoxy)-acetic acid Analogously to example 1.5 and 1.6, but using in the coupling step 5-chloromethyl-4-methyl-2-(4-trifluoromethyl-phenyl)-oxazole (WO01/000603) instead of 5-chloromethyl-4-methyl-2-(4-trifluoromethyl-phenyl)-thiazole, the title compound was obtained as off-white crystals of mp. 156-157° C., MS: 433.0 $(M-H)^-$.

Example 15

15.1) (4-tert-Butoxycarbonylamino-2,6-dimethyl-phenoxy)-acetic acid ethyl ester 4.35 g (19.48 mmol) of (4-amino-2,6-dimethyl-phenoxy)-acetic acid ethyl ester was dissolved in 22 ml of THF, treated with 5.103 g (1.2 eq.) of di-tert-butyl dicarbonate, and refluxed for 1 h. After cooling, the reaction mixture was poured onto crashed ice, extracted twice with EtOAc, the organic layer was washed with water and brine, dried over magnesium sulfate, and evaporated to dryness. Thereby, 6.85 g of the title compound was isolated as reddish solid, sufficiently pure for the next step.

15.2) (4-{tert-Butoxycarbonyl-[4-methyl-2-(4-trifluoromethyl-phenyl)-thiazol-5-ylmethyl]-amino}-2,6-dimethyl-phenoxy)-acetic acid ethyl ester To 0.312 g (0.94 mmol) of the above prepared 4-tert-butoxycarbonylamino-2,6-dimethyl-phenoxy)-acetic acid ethyl ester, dissolved in 4 ml of abs. DMF, were added successively at 0° C. 0.045 g of NaH (60% in mineral oil, 1.2 eq.), 0.140 g (1 eq.) of NaI and 0.273 g (0.96 eq.) of 5-chloromethyl-4-methyl-2-(4-trifluoromethyl-phenyl)-thiazole (WO02/28433). The reaction was allowed to proceed for 5 min at 0° C. and for 0.5 h at ambient temperature. Pouring onto crashed ice/aqueous 10% KHSO4, twofold extraction with EtOAc, washing with water and brine, drying over sodium sulfate, and evaporation of the solvents, followed by flash chromatography (SiO$_2$, hexane/EtOAc=82/18), gave 0.363 g of the title compound as light yellow oil, MS: 579.3 (MH)$^+$.

15.3) (2,6-Dimethyl-4-{[4-methyl-2-(4-trifluoromethyl-phenyl)-thiazol-5-ylmethyl]-amino}-phenoxy)-acetic acid ethyl ester 0.360 g (0.62 mmol) of the above prepared (4-{tert-butoxycarbonyl-[4-methyl-2-(4-trifluoromethyl-phenyl)-thiazol-5-ylmethyl]-amino}-2,6-dimethyl-phenoxy)-acetic acid ethyl ester was dissolved in 6.25 ml of CH$_2$Cl$_2$ and treated dropwise with 1.59 ml of TFA (33 eq.). After additional 30 min at RT, the bulk of the solvents was removed i. V. and the residue distributed between cold NaHCO$_3$-solution and EtOAc. Washing of the organic layer with cold water and brine, drying over magnesium sulfate, and evaporation of the solvents left 0.292 g of the title compound as off-white solid which was used as such for the next step, MS: 479.4 (MH)$^+$.

15.4) (4-{Ethyl-[4-methyl-2-(4-trifluoromethyl-phenyl)-thiazol-5-ylmethyl]-amino}-2,6-dimethyl-phenoxy)-acetic acid ethyl ester 0.102 g (0.21 mmol) of the above prepared (2,6-dimethyl-4-{[4-methyl-2-(4-trifluoromethyl-phenyl)-thiazol-5-ylmethyl]-amino}-phenoxy)-acetic acid ethyl ester was dissolved in 1.5 ml of abs. DMSO and treated with 0.066 g (0.43 mmol) of ethyl iodide and 0.032 g (0.23 mmol) of K$_2$CO$_3$. After vigorously stirring for 18 h at ambient temperature, the reaction mixture was poured onto crashed ice/aqueous 10% KHSO$_4$, extracted twice with EtOAc, the organic layer was washed with water and brine, dried over magnesium sulfate, and evaporated to dryness. Flash chromatography (SiO$_2$, hexane/EtOAc=8/2), yielded finally 0.067 g of the title compound as yellow oil, MS: 507.6 (MH)$^+$.

15.5) (4-{Ethyl-[4-methyl-2-(4-trifluoromethyl-phenyl)-thiazol-5-ylmethyl]-amino}-2,6-dimethyl-phenoxy)-acetic acid 0.66 g (0.13 mmol) of the above prepared (4-{ethyl-[4-methyl-2-(4-trifluoromethyl-phenyl)-thiazol-5-ylmethyl]-amino}-2,6-dimethyl-phenoxy)-acetic acid ethyl ester was dissolved in 0.80 ml of THF/EtOH=1/1, treated with 0.40 ml (3 eq.) of 1N NaOH, and kept at ambient temperature for 1 h. The reaction mixture was then poured onto crashed ice/EtOAc/HCl dil., the organic layer was washed with water and brine, dried over sodium sulfate, and evaporated to dryness. Crystallization from hexane/EtOAc generated finally 0.056 g of the title compound as off-white crystals of mp. 161-162° C., MS: 477.0 (M-H)$^-$.

Example 16

16.1) (4-{tert-Butoxycarbonyl-[4-methyl-2-(4-trifluoromethyl-phenyl)-oxazol-5-ylmethyl]-amino}-2,6-dimethyl-phenoxy)-acetic acid ethyl ester The title compound was prepared in analogy to example 15.2, but using 5-chloromethyl-4-methyl-2-(4-trifluoromethyl-phenyl)-oxazole (WO01/000603) instead of 5-chloromethyl-4-methyl-2-(4-trifluoromethyl-phenyl)-thiazole, as light yellow oil, MS: 563.6 (MH)$^+$.

16.2) (2,6-Dimethyl-4-{[4-methyl-2-(4-trifluoromethyl-phenyl)-oxazol-5-ylmethyl]-amino}-phenoxy)-acetic acid ethyl ester The title compound was prepared in analogy to example 15.3 from the above prepared (4-{tert-butoxycarbonyl-[4-methyl-2-(4-trifluoromethyl-phenyl)-oxazol-5-ylmethyl]-amino}-2,6-dimethyl-phenoxy)-acetic acid ethyl ester as yellowish solid, MS: 463.4 (MH)$^+$.

16.3) (2,6-Dimethyl-4-{methyl-[4-methyl-2-(4-trifluoromethyl-phenyl)-oxazol-5-ylmethyl]-amino}-phenoxy)-acetic acid ethyl ester The title compound was prepared in analogy to example 15.4 from the above prepared (2,6-dimethyl-4-{[4-methyl-2-(4-trifluoromethyl-phenyl)-oxazol-5-ylmethyl]-amino}-phenoxy)-acetic acid ethyl ester, but using methyl iodide as electrophile instead of ethyl iodide, as off-white solid, MS: 477.5 (MH)$^+$.

16.4) (2,6-Dimethyl-4-{methyl-[4-methyl-2-(4-trifluoromethyl-phenyl)-oxazol-5-ylmethyl]-amino}-phenoxy)-acetic acid The title compound was prepared in analogy to example 15.5 from the above prepared (2,6-dimethyl-4-{methyl-[4-methyl-2-(4-trifluoromethyl-phenyl)-oxazol-5-ylmethyl]-amino}-phenoxy)-acetic acid ethyl ester as off-white crystals of mp. 122-123° C., MS: 447.0 (M-H)$^-$.

Example 17

17.1) (2-Methyl-4-nitro-phenoxy)-acetic acid methyl ester

A solution of methyl bromoacetate (15.76 ml, 171 mmol) and 2-methyl-4-nitrophenol (25.0 g, 163 mmol) in dry acetonitrile (300 ml) was treated with Cs$_2$CO$_3$ (61.3 g, 188 mmol) and stirred at RT for 4 h. The mixture was filtered, washed with acetonitrile and evaporated. The residue was suspended in CH$_2$Cl$_2$ (700 ml), filtered and evaporated to give 36.4 g of (2-methyl-4-nitro-phenoxy)-acetic acid methyl ester as yellow crystals, MS: 225 M$^+$.

17.2) (4-Amino-2-methyl-phenoxy)-acetic acid methyl ester

A solution of (2-methyl-4-nitro-phenoxy)-acetic acid methyl ester (36.3 g, 161 mmol) in MeOH (400 ml) and AcOH (11.2 ml, 177 mmol) was hydrogenated in the presence of 10% Pd/C (3.63 g) for 7 h. After removal of the catalyst the reaction was evaporated, dissolved in toluene and evaporated (5×) to give 32.5 g of (4-amino-2-methyl-phenoxy)-acetic acid methyl ester as a brown crystallin residue, MS: 196 (MH$^+$).

17.3) (4-tert-Butoxycarbonylamino-2-methyl-phenoxy)-acetic acid methyl ester

A solution of (4-amino-2-methyl-phenoxy)-acetic acid methyl ester (21.1 g, 108 mmol) in THF (210 ml) was treated with di-tert-butyl dicarbonate (24.7 g, 111 mmol) and heated for 3 h at 80° C. The solution was evaporated and purified by flash chromatography with a gradient of n-heptane:EtOAc 9:1 to 4:1 to yield 28.1 g of (4-tert-butoxycarbonylamino-2-methyl-phenoxy)-acetic acid methyl ester as a light pink crystalline residue, MS: 295 M$^+$.

17.4) [4-(tert-Butoxycarbonyl-methyl-amino)-2-methyl-phenoxy]-acetic acid methyl ester To an ice-cooled and stirred solution of (4-tert-butoxycarbonylamino-2-methyl-phenoxy)-acetic acid methyl ester (22.8 g, 77 mmol) in DMF (230 ml) was added within 10 min NaH (3.7 g, 55% in oil, 85 mmol) and after 1 h, CH$_3$I (14.5 ml, 232 mmol). The reaction was stirred at 0° C. for 2 h, neutralized with aqueous 10% KHSO$_4$ and extracted with aqueous 10% KHSO$_4$/Et$_2$O (3×). The organic phases were washed with aqueous 10% NaCl, dried (Na$_2$SO$_4$) and evaporated to give 25.8 g of [4-(tert-butoxycarbonyl-methyl-amino)-2-methyl-phenoxy]-acetic acid methyl ester, MS: 310 (MH$^+$).

17.5) (2-Methyl-4-methylamino-phenoxy)-acetic acid methyl ester

A solution of crude [4-(tert-butoxycarbonyl-methyl-amino)-2-methyl-phenoxy]-acetic acid methyl ester (25.8 g, 77 mmol) in CH$_2$Cl$_2$ (600 ml) was treated at 0° C. with TFA (198 ml) and stirred at RT for 30 min. The reaction was evaporated, treated with chilled aqueous saturated NaHCO$_3$ solution/Et$_2$O (3×). The organic phases were washed with aqueous 10% NaCl, dried (Na$_2$SO$_4$) and evaporated to give 16.2 g of crude (2-methyl-4-methylamino-phenoxy)-acetic acid methyl ester. Purification by flash chromatography with a gradient of n-heptane:EtOAc 9:1 to 4:1 yielded 12.7 g of (2-methyl-4-methylamino-phenoxy)-acetic acid methyl ester as an orange oil, MS: 210 (MH$^+$).

17.6) (R,S)-[2-Methyl-4-(methyl-{1-[2-(4-trifluoromethyl-phenyl)-thiazol-5-yl]-ethyl}-amino)-phenoxy]-acetic acid methyl ester A suspension of potassium carbonate (106 mg, 0.77 mmol), sodium iodide (105 mg, 0.70 mmol) and of (2-methyl-4-methylamino-phenoxy)-acetic acid methyl ester (146 mg, 0.70 mmol) in DMSO (4.2 ml) was treated with (R,S)-5-(1-chloro-ethyl)-2-(4-trifluoromethyl-phenyl)-thiazole (204 mg, 0.70 mmol, example 17.8) in 3 portions over 2 h. The reaction mixture was stirred for total 16 h at RT, taken up in ether and washed with KHSO$_4$-solution (10%). The organic phase was washed with NaCl (10%), dried (Na$_2$SO$_4$) and evaporated. Purification by flash chromatography (SiO$_2$, n-heptane/AcOEt=9/1) gave 161 mg of pure (R,S)-[2-methyl-4-(methyl-{1-[2-(4-trifluoromethyl-phenyl)-thiazol-5-yl]-ethyl}-amino)-phenoxy]-acetic acid methyl ester, MS: 465.4 (MH)$^+$.

17.7) (R,S)-[2-Methyl-4-(methyl-{1-[2-(4-trifluoromethyl-phenyl)-thiazol-5-yl]-ethyl}-amino)-phenoxy]-acetic acid A solution of (R,S)-[2-methyl-4-(methyl-{1-[2-(4-trifluoromethyl-phenyl)-thiazol-5-yl]-ethyl}-amino)-phenoxy]-acetic acid methyl ester (148 mg, 0.32 mmol) in THF (0.96 ml) and ethanol (1 ml) was treated at 0° C. with 1N LiOH (0.96 ml) and stirred for 1 h at RT. The reaction was extracted with aqueous 10% KHSO$_4$/Et$_2$O (3×). The organic phase was washed with aqueous 10% NaCl, dried over Na$_2$SO$_4$ and evaporated to give pure (R,S)-[2-methyl-4-(methyl-{1-[2-(4-trifluoromethyl-phenyl)-thiazol-5-yl]-ethyl}-amino)-phenoxy]-acetic acid, MS: 449.1 (M-H)$^-$.

The reagent used in 17.6) was synthesized as follows:

17.8) (R,S)-5-(1-Chloro-ethyl)-2-(4-trifluoromethyl-phenyl)-thiazole

Analogously, to example 3.3), (R,S)-1-[2-(4-trifluoromethyl-phenyl)-thiazol-5-yl]-ethanol (WO02/062774) gave (R,S)-5-(1-chloro-ethyl)-2-(4-trifluoromethyl-phenyl)-thiazole, MS: 291 (M$^+$, 1Cl).

Example 18

18.1) (4-{tert-Butoxycarbonyl-[4-methyl-2-(4-trifluoromethyl-phenyl)-thiazol-5-ylmethyl]-amino}-2-methyl-phenoxy)-acetic acid methyl ester To an ice-cooled and stirred solution of (4-tert-butoxycarbonylamino-2-methyl-phenoxy)-acetic acid methyl ester (1.00 g, 3.39 mmol, example 17.3), sodium iodide (0.51 g, 3.39 mmol) and 5-chloromethyl-4-methyl-2-(4-trifluoromethyl-phenyl)-thiazole (1.09 g, 3.72 mmol, WO02/28433) in DMF (10 ml) was added within 10 min NaH (0.19 g, 55% in oil, 4.40 mmol). The reaction was stirred at 0° C. for 2 h, 30 min at RT and then neutralized with chilled aqueous 10% KHSO$_4$ and extracted with aqueous 10% KHSO$_4$/Et$_2$O (3×). The organic phases were washed with aqueous 10% NaCl, dried (Na$_2$SO$_4$) and evaporated to give 2.14 g of (4-{tert-butoxycarbonyl-[4-methyl-2-(4-trifluoromethyl-phenyl)-thiazol-5-ylmethyl]-amino}-2-methyl-phenoxy)-acetic acid methyl ester, MS: 551.3 (MH$^+$).

18.2) (2-Methyl-4-{[4-methyl-2-(4-trifluoromethyl-phenyl)-thiazol-5-ylmethyl]-amino}-phenoxy)-acetic acid methyl ester A solution of crude (4-{tert-butoxycarbonyl-[4-methyl-2-(4-trifluoromethyl-phenyl)-thiazol-5-ylmethyl]-amino}-2-methyl-phenoxy)-acetic acid methyl ester (2.1 g containing 1.83 g, 3.32 mmol) in CH$_2$Cl$_2$ (33 ml) was treated at 0° C. with TFA (12.7 ml) and stirred at RT for 45 min. The reaction was evaporated, treated with chilled aqueous saturated NaHCO$_3$ solution/Et$_2$O (3×). The organic phases were washed with aqueous 10% NaCl, dried (Na$_2$SO$_4$) and evaporated. Purification by flash chromatography with a gradient of n-heptane:EtOAc 95:5 to 4:1 yielded 0.34 g of (2-methyl-4-{[4-methyl-2-(4-trifluoromethyl-phenyl)-thiazol-5-ylmethyl]-amino}-phenoxy)-acetic acid methyl ester as an light yellow solid, MS: 451.3 (MH$^+$).

18.3) (2-Methyl-4-{[4-methyl-2-(4-trifluoromethyl-phenyl)-thiazol-5-ylmethyl]-amino}-phenoxy)-acetic acid A solution of (2-methyl-4-{[4-methyl-2-(4-trifluoromethyl-phenyl)-thiazol-5-ylmethyl]-amino}-phenoxy)-acetic acid methyl ester (330 mg, 0.73 mmol) in THF (2.2 ml) and ethanol (2.2 ml) was treated at 0° C. with 1N LiOH (2.2 ml) and stirred for 1.25 h at RT. The reaction was extracted with aqueous 10% KHSO$_4$/Et$_2$O (3×). The organic phase was washed with aqueous 10% NaCl, dried over Na$_2$SO$_4$ and evaporated. The product was crystallized from CH$_2$Cl$_2$/Et$_2$O to give pure (2-methyl-4-{[4-methyl-2-(4-trifluoromethyl-phenyl)-thiazol-5-ylmethyl]-amino}-phenoxy)-acetic acid, MS: 437.4 (MH)$^+$, MP: 201-203° C., dec.

Example 19

19.1) (4-{Ethyl-[4-methyl-2-(4-trifluoromethyl-phenyl)-thiazol-5-ylmethyl]-amino}-2-methyl-phenoxy)-acetic acid methyl ester A suspension of potassium carbonate (76 mg, 0.55 mmol), and (2-methyl-4-{[4-methyl-2-(4-trifluoromethyl-phenyl)-thiazol-5-ylmethyl]-amino}-phenoxy)-acetic acid methyl ester (225 mg, 0.50 mmol, example 18.2) in DMSO (3 ml) was treated with iodoethane (0.04 ml, 0.53 mmol) in DMSO (0.5 ml) and stirred for 19 h at RT. Again iodoethane (0.34 ml, 4.20 mmol) in 2 portions over 7 h was added. The reaction mixture was taken up in ether and washed with KHSO$_4$-solution (10%). The organic phase was washed with NaCl (10%), dried (Na$_2$SO$_4$) and evaporated. Purification by flash chromatography (SiO$_2$, n-heptane/AcOEt=9/1) gave 141 mg of pure (4-{ethyl-[4-methyl-2-(4-trifluoromethyl-phenyl)-thiazol-5-ylmethyl]-amino}-2-methyl-phenoxy)-acetic acid methyl ester, MS: 479.5 (MH)$^+$.

19.2) (4-{Ethyl-[4-methyl-2-(4-trifluoromethyl-phenyl)-thiazol-5-ylmethyl]-amino}-2-methyl-phenoxy)-acetic acid Analogously, to example 18.3), (4-{ethyl-[4-methyl-2-(4-trifluoromethyl-phenyl)-thiazol-5-ylmethyl]-amino}-2-methyl-phenoxy)-acetic acid methyl ester gave (4-{ethyl-[4-methyl-2-(4-trifluoromethyl-phenyl)-thiazol-5-ylmethyl]-amino}-2-methyl-phenoxy)-acetic acid, MS: 465.4 (MH)$^+$, MP: 147-154° C., slow dec.

Example 20

20.1) (2-Iodo-phenoxy)-acetic acid methyl ester

Analogously, to example 1.1), methyl bromoacetate and 2-iodophenol gave (2-iodo-phenoxy)-acetic acid methyl ester, MS: 292.0 (M$^+$).

20.2) (2-Iodo-4-nitro-phenoxy)-acetic acid methyl ester

Analogously, to example 13.4), (2-iodo-phenoxy)-acetic acid methyl ester gave (2-iodo-4-nitro-phenoxy)-acetic acid methyl ester, MS: 336.9 (M$^+$).

20.3) (4-Amino-2-iodo-phenoxy)-acetic acid methyl ester

NH$_4$Cl (4.49 g, 84.00 mmol) in water (105 ml) was added to a suspension of Fe (powder, 2.85 g, 51.00 mmol) in water (18 ml), the treated with (2-iodo-4-nitro-phenoxy)-acetic acid methyl ester (5.06 g, 15.00 mmol) in MeOH (105 ml). The reaction was heated at 90° C. for 28 h, filtered and extracted with brine/EtOAc (3×). The organic phase was washed with brine, dried over Na$_2$SO$_4$ and evaporated to give 1.2 g of (4-amino-2-iodo-phenoxy)-acetic acid methyl ester, MS: 308.1 (MH)$^+$.

20.4) (4-tert-Butoxycarbonylamino-2-iodo-phenoxy)-acetic acid methyl ester

Analogously, to example 17.3), (4-amino-2-iodo-phenoxy)-acetic acid methyl ester gave (4-tert-butoxycarbonylamino-2-iodo-phenoxy)-acetic acid methyl ester, MS: 325.4 (M+NH$_4$)$^+$.

20.5) [4-(tert-Butoxycarbonyl-methyl-amino)-2-iodo-phenoxy]-acetic acid methyl ester Analogously, to example 17.4), (4-tert-butoxycarbonylamino-2-iodo-phenoxy)-acetic acid methyl ester gave [4-(tert-butoxycarbonyl-methyl-amino)-2-iodo-phenoxy]-acetic acid methyl ester, MS: 421 (M$^+$).

20.6) (2-Iodo-4-methylamino-phenoxy)-acetic acid methyl ester

Analogously, to example 17.5), [4-(tert-butoxycarbonyl-methyl-amino)-2-iodo-phenoxy]-acetic acid methyl ester gave (2-iodo-4-methylamino-phenoxy)-acetic acid methyl ester, MS: 322.2 (MH)$^+$.

20.7) (2-Iodo-4-{methyl-[4-methyl-2-(4-trifluoromethyl-phenyl)-thiazol-5-ylmethyl]-amino}-phenoxy)-acetic acid methyl ester A suspension of potassium carbonate (45 mg, 0.33 mmol), sodium iodide (45 mg, 0.30 mmol) and of (2-iodo-4-methylamino-phenoxy)-acetic acid methyl ester (73 mg, 0.35 mmol) in DMSO (4 ml) was treated with 5-chloromethyl-4-methyl-2-(4-trifluoromethyl-phenyl)-thiazole (96 mg, 0.30 mmol, WO02/28433) in 3 portions over 1.5 h. The reaction mixture was stirred for total 2.5 h at RT, taken up in ether and washed with KHSO$_4$-solution (10%). The organic phase was washed with NaCl (10%), dried (Na$_2$SO$_4$) and evaporated. Purification by flash chromatography (SiO$_2$, n-heptane/AcOEt=4/1) gave 151 mg of pure (2-iodo-4-{methyl-[4-methyl-2-(4-trifluoromethyl-phenyl)-thiazol-5-ylmethyl]-amino}-phenoxy)-acetic acid methyl ester, MS: 577.2 (MH)$^+$.

20.8) (2-Iodo-4-{methyl-[4-methyl-2-(4-trifluoromethyl-phenyl)-thiazol-5-ylmethyl]-amino}-phenoxy)-acetic acid A solution of (2-iodo-4-{methyl-[4-methyl-2-(4-trifluoromethyl-phenyl)-thiazol-5-ylmethyl]-amino}-phenoxy)-acetic acid methyl ester (140 mg, 0.24 mmol) in THF (1.2 ml) and ethanol (1.2 ml) was treated at 0° C. with 1N LiOH (0.73 ml) and stirred for 3 h at RT. The reaction was extracted with aqueous 10% KHSO$_4$/Et$_2$O (3×). The organic phase was washed with aqueous 10% NaCl, dried over Na$_2$SO$_4$ and evaporated. The product was crystallized from CH$_2$Cl$_2$ to give 79 mg of pure (2-iodo-4-{methyl-[4-methyl-2-(4-trifluoromethyl-phenyl)-thiazol-5-ylmethyl]-amino}-phenoxy)-acetic acid, MS: 561.1 (M-H)$^-$, MP: 172.5-173.0° C.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed is:

1. A compound of the formula

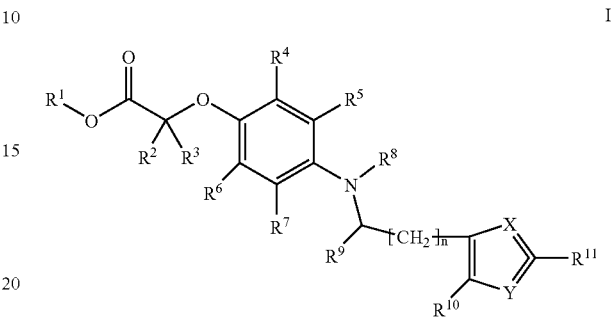

wherein:

X is S and Y is N;

$R^1$ is hydrogen or $C_{1-7}$-alkyl;

$R^2$ and $R^3$ independently from each other are selected from the group consisting of hydrogen, $C_{1-7}$-alkyl and $C_{1-7}$-alkoxy;

$R^4$, $R^5$, $R^6$ and $R^7$ independently from each other are selected from the group consisting of hydrogen, $C_{1-7}$-alkyl, $C_{3-7}$-cycloalkyl, halogen, $C_{1-7}$-alkoxy, $C_{1-7}$-alkyl-$C_{1-7}$-alkoxy-$C_{1-7}$-alkyl, $C_{2-7}$-alkenyl, $C_{2-7}$-alkinyl, fluoro-$C_{1-7}$-alkyl and cyano;

$R^8$ is selected from the group consisting of hydrogen, $C_{1-7}$-alkyl, $C_{3-7}$-cycloalkyl and fluoro-$C_{1-7}$-alkyl;

$R^9$ is selected from the group consisting of hydrogen, $C_{1-7}$-alkyl, $C_{2-7}$-alkinyl, $C_{3-7}$-cycloalkyl and fluoro-$C_{1-7}$-alkyl;

$R^{10}$ is selected from the group consisting of hydrogen, $C_{1-7}$-alkyl, $C_{2-7}$-alkinyl, $C_{3-7}$-cycloalkyl and fluoro-$C_{1-7}$-alkyl;

$R^{11}$ is aryl;

n is 0, 1 or 2;

or an enantiomer thereof or a pharmaceutically acceptable salt thereof or a pharmaceutically acceptable ester thereof.

2. A compound of claim 1 wherein $R^1$ is hydrogen.

3. A compound of claim 2 wherein $R^2$ and $R^3$ are hydrogen.

4. A compound of claim 3, wherein $R^4$ is selected from the group consisting of hydrogen, $C_{1-7}$-alkyl, $C_{3-7}$-cycloalkyl, halogen, $C_{1-7}$-alkoxy, $C_{1-7}$-alkyl-$C_{1-7}$-alkoxy-$C_{1-7}$-alkyl, $C_{2-7}$-alkenyl, $C_{2-7}$-alkinyl, fluoro-$C_{1-7}$-alkyl or cyano, and $R^5$, $R^6$ and $R^7$ are hydrogen.

5. A compound of claim 4, wherein $R^4$ is selected from the group consisting of hydrogen, $C_{1-7}$-alkyl, halogen, $C_{1-6}$-alkoxy or fluoro-$C_{1-7}$-alkyl.

6. A compound of claim 5, wherein $R^4$ is selected from the group consisting of $C_{1-7}$-alkyl, halogen or fluoro-$C_{1-7}$-alkyl.

7. A compound of claim 6, wherein $R^8$ is hydrogen or $C_{1-7}$-alkyl.

8. A compound of claim 7, wherein $R^8$ is methyl.

9. A compound of claim 8, wherein $R^9$ is hydrogen or $C_{1-7}$-alkyl.

10. A compound of claim 9, wherein $R^{10}$ is hydrogen or $C_{1-7}$-alkyl.

11. A compound of claim 10, wherein $R^{10}$ is methyl.

12. A compound of claim 1, wherein $R^{11}$ is unsubstituted phenyl or phenyl substituted with one to three groups selected from the group consisting of $C_{1-7}$-alkyl, $C_{1-7}$-alkoxy, halogen, fluoro-$C_{1-7}$-alkyl and cyano.

13. A compound of claim 12, wherein $R^{11}$ is phenyl substituted with halogen or fluoro-$C_{1-7}$-alkyl.

14. A compound of claim 13, wherein $R^{11}$ is 4-trifluoromethylphenyl.

15. A compound of claim 1, selected from the group consisting of:
(2-methyl-4-{methyl-[4-methyl-2-(4-trifluoromethyl-phenyl)-thiazol-5-ylmethyl]-amino}-phenoxy)-acetic acid;
(2-chloro-4-{methyl-[4-methyl-2-(4-trifluoromethyl-phenyl)-thiazol-5-ylmethyl]-amino}-phenoxy)-acetic acid;
(2-fluoro-4-{methyl-[4-methyl-2-(4-trifluoromethyl-phenyl)-thiazol-5-ylmethyl]-amino}-phenoxy)-acetic acid;
(4-{methyl-[4-methyl-2-(4-trifluoromethyl-phenyl)-thiazol-5-ylmethyl]-amino}-2-trifluoromethyl-phenoxy)-acetic acid; and
(2-ethyl-4-{methyl-[4-methyl-2-(4-trifluoromethyl-phenyl)-thiazol-5-ylmethyl]-amino}-phenoxy)-acetic acid.

16. A compound of claim 1, selected from the group consisting of
(2-(3-methoxy-propyl)-4-{methyl-[4-methyl-2-(4-trifluoromethyl-phenyl)-thiazol-5-ylmethyl]-amino}-phenoxy)-acetic acid, and
(2-methyl-4-{[4-methyl-2-(4-trifluoromethyl-phenyl)-thiazol-5-ylmethyl]-amino}-phenoxy)-acetic acid.

17. A compound of claim 1, selected from the group consisting of
(2-methyl-4-{methyl-[4-methyl-2-(4-trifluoromethyl-phenyl)-thiazol-5-ylmethyl]-amino}-phenoxy)-acetic acid;
(2-methyl-4-{methyl-[2-(4-trifluoromethyl-phenyl)-thiazol-5-ylmethyl]-amino}-phenoxy)-acetic acid;
[2-methyl-4-(methyl-{1-[4-methyl-2-(4-trifluoromethyl-phenyl)-thiazol-5-yl]-ethyl}-amino)-phenoxy]-acetic acid;
(2-chloro-4-{methyl-[4-methyl-2-(4-trifluoromethyl-phenyl)-thiazol-5-ylmethyl]-amino}-phenoxy)-acetic acid;
(2-fluoro-4-{methyl-[4-methyl-2-(4-trifluoromethyl-phenyl)-thiazol-5-ylmethyl]-amino}-phenoxy)-acetic acid;
(4-{methyl-[4-methyl-2-(4-trifluoromethyl-phenyl)-thiazol-5-ylmethyl]-amino}-2-trifluoromethyl-phenoxy)-acetic acid;
(2-ethyl-4-{methyl-[4-methyl-2-(4-trifluoromethyl-phenyl)-thiazol-5-ylmethyl]-amino}-phenoxy)-acetic acid;
(2-methoxy-4-{methyl-[4-methyl-2-(4-trifluoromethyl-phenyl)-thiazol-5-ylmethyl]-amino}-phenoxy)-acetic acid;
(4-{ethyl-[4-methyl-2-(4-trifluoromethyl-phenyl)-thiazol-5-ylmethyl]-amino}-phenoxy)-acetic acid;
(4-{ethyl-[2-(4-trifluoromethyl-phenyl)-thiazol-5-ylmethyl]-amino}-phenoxy)-acetic acid;
(4-{[4-methyl-2-(4-trifluoromethyl-phenyl)-thiazol-5-ylmethyl]-amino}-phenoxy)-acetic acid;
(4-{methyl-[4-methyl-2-(4-trifluoromethyl-phenyl)-thiazol-5-ylmethyl]-amino}-phenoxy)-acetic acid;
(2-(3-methoxy-propyl)-4-{methyl-[4-methyl-2-(4-trifluoromethyl-phenyl)-thiazol-5-ylmethyl]-amino}-phenoxy)-acetic acid;
(2-methyl-4-{methyl-[4-methyl-2-(4-trifluoromethyl-phenyl)-oxazol-5-ylmethyl]-amino}-phenoxy)-acetic acid;
(4-{ethyl-[4-methyl-2-(4-trifluoromethyl-phenyl)-thiazol-5-ylmethyl]-amino}-2,6-dimethyl-phenoxy)-acetic acid;
(2,6-dimethyl-4-{methyl-[4-methyl-2-(4-trifluoromethyl-phenyl)-oxazol-5-ylmethyl]-amino}-phenoxy)-acetic acid;
(R,S)-[2-methyl-4-(methyl-{1-[2-(4-trifluoromethyl-phenyl)-thiazol-5-yl]-ethyl}-amino)-phenoxy]-acetic acid;
(2-methyl-4-{[4-methyl-2-(4-trifluoromethyl-phenyl)-thiazol-5-ylmethyl]-amino}-phenoxy)-acetic acid;
(4-{ethyl-[4-methyl-2-(4-trifluoromethyl-phenyl)-thiazol-5-ylmethyl]-amino}-2-methyl-phenoxy)-acetic acid; and
(2-iodo-4-{methyl-[4-methyl-2-(4-trifluoromethyl-phenyl)-thiazol-5-ylmethyl]-amino}-phenoxy)-acetic acid.

18. A process for the manufacture of a compound of claim 1, which process comprises
reacting a compound of formula

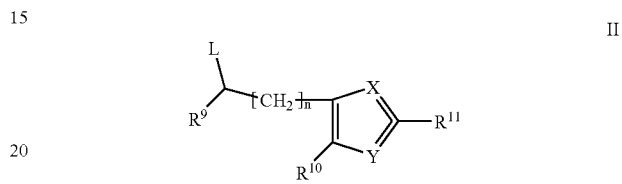

wherein L is a leaving group and X, Y, $R^9$, $R^{10}$, $R^{11}$ and n are as defined as in claim 1, with an aniline derivative of formula

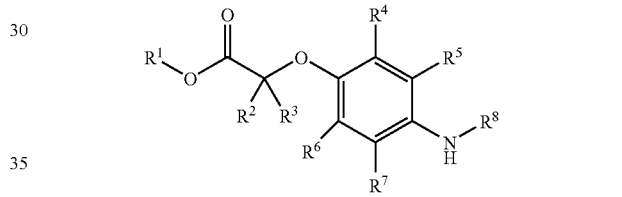

wherein $R^1$ is $C_{1-7}$-alkyl and $R^2$ to $R^8$ are as defined in claim 1, to obtain a compound of formula

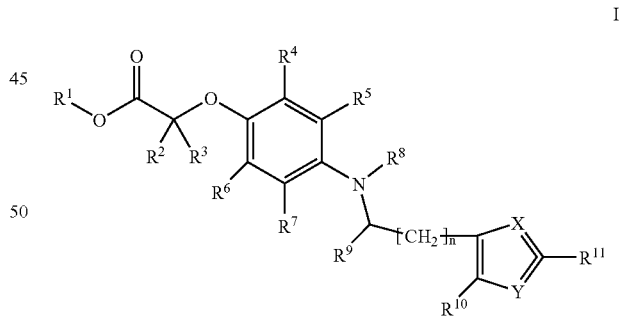

wherein $R^1$ is $C_{1-7}$-alkyl,
and thereafter optionally hydrolyzing the ester group to obtain a compound of formula I, wherein $R^1$ is hydrogen.

19. A pharmaceutical composition comprising a compound of claim 1.

* * * * *